(12) United States Patent
Kolios et al.

(10) Patent No.: US 8,192,362 B2
(45) Date of Patent: Jun. 5, 2012

(54) METHODS OF MONITORING CELLULAR DEATH USING LOW FREQUENCY ULTRASOUND

(75) Inventors: Michael Kolios, Ancaster (CA); Gregory J. Czarnota, Oakville (CA); Michael D. Sherar, Toronto (CA); Adam Tunis, Ottawa (CA); John Hunt, Toronto (CA)

(73) Assignee: Sunnybrook Health Sciences Centre (CA)

( * ) Notice: Subject to any disclaimer, the term of this patent is extended or adjusted under 35 U.S.C. 154(b) by 1204 days.

(21) Appl. No.: 11/455,005

(22) Filed: Jun. 15, 2006

(65) Prior Publication Data

US 2007/0167755 A1 Jul. 19, 2007

Related U.S. Application Data

(60) Provisional application No. 60/691,577, filed on Jun. 16, 2005.

(51) Int. Cl.
*A61B 8/00* (2006.01)
(52) U.S. Cl. .................. 600/438; 600/437; 600/443
(58) Field of Classification Search .......... 600/437–439, 600/443
See application file for complete search history.

(56) References Cited

U.S. PATENT DOCUMENTS

| | | | | |
|---|---|---|---|---|
| 5,657,760 | A | 8/1997 | Ying et al. | 128/999 |
| 6,511,430 | B1 | 1/2003 | Sherar et al. | 600/443 |
| 6,585,647 | B1 | 7/2003 | Winder | 546/181 |
| 6,716,412 | B2 * | 4/2004 | Unger | 424/9.52 |
| 7,662,097 | B2 * | 2/2010 | Falco et al. | 600/437 |
| 2006/0064014 | A1 | 3/2006 | Falco et al. | 600/439 |
| 2008/0033296 | A1 * | 2/2008 | Isern | 600/439 |
| 2008/0255461 | A1 * | 10/2008 | Weersink et al. | 600/476 |
| 2008/0319375 | A1 * | 12/2008 | Hardy | 604/22 |
| 2010/0099989 | A1 * | 4/2010 | Falco et al. | 600/443 |
| 2010/0113861 | A1 * | 5/2010 | Biris et al. | 600/10 |

FOREIGN PATENT DOCUMENTS

| | | |
|---|---|---|
| WO | WO2006032124 A1 | 3/2006 |
| WO | WO2007063425 A2 | 6/2007 |

OTHER PUBLICATIONS

BI Raju, MA Srinivasan. Statistics of Envelope of High-Frequency Ultrasonic Backscatter from Human Skin In Vivo. IEEE Transactions on Ultrasonics, Ferroelectrics, and Frequency Control. Jul. 2002, 49(7): 871-882.*

Baddour, et al., High frequency ultrasound scattering from microspheres and single cells. Master's thesis, University of Toronto, 2004.

(Continued)

*Primary Examiner* — Brian Casler
*Assistant Examiner* — Amanda Lauritzen
(74) *Attorney, Agent, or Firm* — Lynn C. Schumacher; Bacon & Thomas, PLLC

(57) ABSTRACT

A method of detecting cellular damage within a subject comprises transmitting low frequency ultrasound (20 MHz or below) into a selected site within the subject wherein the selected site has been exposed to a stress capable of causing cellular death at the selected site. At least a portion of ultrasound backscattered from the ultrasound transmitted into the selected site is received. The received backscattered ultrasound is compared to a control backscatter measurement. An increase or a decrease in intensity or spectral slope of the received backscattered ultrasound when compared to the control backscatter measurement indicates cellular death or damage at the selected site within the subject.

20 Claims, 30 Drawing Sheets

OTHER PUBLICATIONS

Barry, et al., Activation of programmed cell death (apoptosis) by cisplatin, other anticancer drugs, toxins and hyperthermia. *Biochem Pharmacol*, 40(10):2353-2362, 1990.

Beaulieu, et al., High-frequency ultrasound characterization of microcellular components. In *Proceedings of the 10th Congress of the World Federation for Ultrasound in Medicine and Biology*, p. S123, Montreal, Canada, 2003.

Berube, et al., Use of a high frequency ultrasound microscope to image the action of 2-nitroimidazoles in multicellular spheroids. *Br J Cancer*, 65(5):633-640, 1992.

Czarnota, et al., Ultrasonic biomicroscopy of viable, dead and apoptotic cells. *Ultrasound Med Biol*, 23(6):961-965, 1997.

Czarnota, et al., Ultrasound imaging of apoptosis. Damage effects visualized. *Methods Mol Biol*, 203:257-277, 2002.

Czarnota, et al., Ultrasound imaging of apoptosis: high-resolution non-invasive monitoring of programmed cell death in vitro, in situ and in vivo. *Br J Cancer*, 81(3):520-527, 1999.

Czarnota, Ultrasound imaging of apoptosis in vivo: Effects of subcellular nuclear morphology and cell membrane morphology. In *Proceedings of the 10th Congress of the World Federation for Ultrasound in Medicine and Biology*, p. S117, Montreal, Canada, 2003.

Dutt, et al., Ultrasound echo envelope analysis using a homodyned k distribution signal model. *Ultrason Imaging*, 16(4):265-287, 1994.

Faran, Sound scattering by solid cylinders and spheres. *J Acoust Soc Am*, 23(4):405-418, 1951.

Farnoud, N.R.; Kolios, M.; Krishnan, S., Ultrasound backscatter signal characterization and classification using autoregressive modeling and machine learning algorithms. *Engineering in Medicine and Biology Society, 2003. Proceedings of the 25th Annual International Conference of the IEEE*, vol. 3, Issue, Sep. 17-21, 2003 pp. 2861-2864.

Foster, et al., Advances in ultrasound biomicroscopy. *Ultrasound Med Biol*, 26(1):1-27, 2000.

Hall et al., Describing small-scale structure in random media using pulse echo ultrasound, *Journal of the Acoustical Society of America*, 87(1):179-192, 1990.

Hao, et al., Characterization of reperfused infarcted myocardium from high-frequency intracardiac ultrasound imaging using homodyned k distribution. *IEEE Trans Ultrason Ferroelectr Freq Control*, 49(11):1530-1542, 2002.

Hao, et al., Identification of reperfused infarcted myocardium from high frequency intracardiac ultrasound images using homodyned k distribution. In *IEEE Ultrasonics Symposium*, pp. 1189-1192, 2001.

Hao, et al., Segmenting high-frequency intracardiac ultrasound images of myocardium into infarcted, ischemic, and normal regions. *IEEE Trans Med Imaging*, 20(12):1373-1383, 2001.

Harvey, et al., "Advances in ultrasound," *Clin Radiol*, 57(3):157-177, 2002.

Hunt, et al., A model based upon pseudo regular spacing of cells combined with the randomisation of the nuclei can explain the significant changes in high-frequency ultrasound signals during apoptosis. *Ultrasound Med Biol*, 28(2):217-226, 2002.

Insana, et al., Parametric ultrasound imaging from backscatter coefficient measurements: Image formation and interpretation, *Ultrasonic Imaging*, 12(4):245-267,1990.

Insana, et al., Describing small-scale structure in random media using pulse-echo ultrasound, *J Acoust Soc Am*, 87(1):179-92, 1990.

Jenderka, K.-V.; Gersing, E., Comparison of impedance and ultrasound spectroscopy in investigations of ischaemia caused alterations in organ tissue. *Engineering in Medicine and Biology Society, 1996. Bridging Disciplines for Biomedicine. Proceedings of the 18th Annual International Conference of the IEEE*, vol. 2, Issue, Oct. 31-Nov. 3, 1996 pp. 855-856.

Kolios, et al., An investigation of backscatter power spectra from cells, cell pellets and microspheres. In *IEEE Ultrasonics Symposium*, pp. 752-757, Honolulu, HI, 2003.

Kolios, et al., Analysis of ultrasound backscatter from ensembles of cells and isolated nuclei. In *IEEE Ultrasonics Symposium*, vol. 2, pp. 1257-1260, 2001.

Kolios, et al., Towards understanding the nature of high frequency backscatter from cells and tissues: An investigation of backscatter power spectra from different concentrations of cells of different sizes. In *IEEE Ultrasonics Symposium*, Montreal, Canada, p. 606-609, 2004.

Kolios, et al., Ultrasonic spectral parameter characterization of apoptosis. *Ultrasound Med Biol*, 28(5):589-597, 2002.

Lizzi, et al., Theoretical framework for spectrum analysis in ultrasonic tissue characterization, *Journal of the Acoustical Society of America*, 73(4):1366-1373, 1983.

Mo and Cobbold, A unified approach to modeling the backscattered doppler ultrasound from blood. *IEEE Trans Biomed Eng*, 39(5):450-461, 1992.

Molthen, et al., Comparisons of the rayleigh and k-distribution models using in vivo breast and liver tissue. *Ultrasound Med Biol*, 24(1):93-100, 1998.

Molthen, et al., Using phase information in ultrasonic backscatter for in vivo liver analysis, *Ultrasound Med Biol*, 24(1):79-91, 1998.

Oelze, et al., Differentiation of tumor types in vivo by scatterer property estimates and parametric images using ultrasound backscatter. In *IEEE Trans Ultrason Ferroelectr Freq Control*, Honolulu, Hi, 2003. IEEE.

Oelze, et al., Method of improved scatterer size estimation and application to parametric imaging using ultrasound. *J Acoust Soc Am*, 112(6):3053-3063, 2002.

Oelze, et al., Parametric imaging of rat mammary tumors in vivo for the purposes of tissue characterization. *J Ultrasound Med*, 21(11):1201-1210, 2002.

Raju and Srinivasan, Statistics of envelope of high-frequency ultrasonic backscatter from human skin in vivo. *IEEE Trans Ultrason Ferroelectr Freq Control*, 49(7):871-882, 2002.

Shankar, A compound scattering pdf for the ultrasonic echo envelope and its relationship to k and nakagarni distributions. *IEEE Trans Ultrason Ferroelectr Freq Control*, 50(3):339-343, 2003.

Shankar, et al., Classification of breast masses in ultrasonic b scans using nakagami and k distributions. *Phys Med Biol*, 48(14):2229-2240, 2003.

Shankar, et al., Classification of ultrasonic b-mode images of breast masses using nakagami distribution. *IEEE Trans Ultrason Ferroelectr Freq Control*, 48(2):569-580, 2001.

Shankar, et al., Studies on the use of non-rayleigh statistics for ultrasonic tissue characterization. *Ultrasound Med Biol*, 22(7):873-882, 1996.

Shankar, et al., Use of non-rayleigh statistics for the identification of tumors in ultrasonic b-scans of the breast. *IEEE Trans Med Imaging*, 12(4):687-692, 1993.

Shankar. A model for ultrasonic scattering from tissues based on the k distribution. *Phys Med Biol*, 40(10):1633-1649, 1995.

Shankar. Ultrasonic tissue characterization using a generalized nakagami model. *IEEE Trans Ultrason Ferroelectr Freq Control*, 48(6):1716-1720, 2001.

Sherar, et al., A 100 mhz b-scan ultrasound backscatter microscope. *Ultrason Imaging*, 11(2):95-105, 1989.

Sherar, et al., Ultrasound backscatter microscopy images the internal structure of living tumour spheroids. *Nature*, 330(6147):493-495, 1987.

Stacy, A generalization of the gamma distribution. *The Annals of Mathematical Statistics*, 33(3):1187-1192, 1962.

Tunis, et al., High frequency ultrasound signal statistics from mouse mammary tissue during involution. In *IEEE Ultrasonics Symposium*, Montreal, Canada, 2004.

Tunis, et al., Monitoring structural changes in cells with high—frequency ultrasound signal statistics, *Ultrasound Med Biol.*, 31(8):1041-1049, 2005 (abstract).

Tunis, Monitoring Structural Changes in Cells and Tissues with High Frequency Ultrasound Signal Statistics, Thesis, 2005.

\* cited by examiner

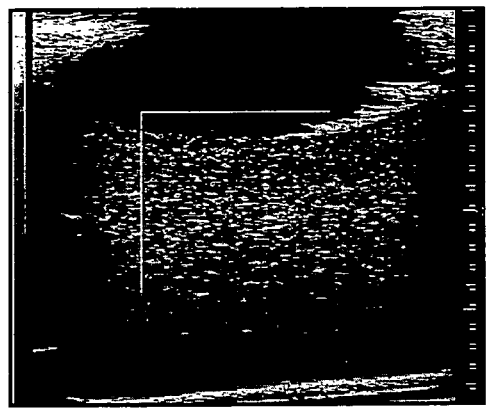
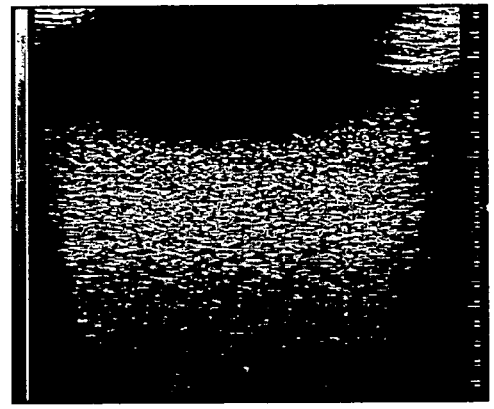
FIG.2A                FIG.2B
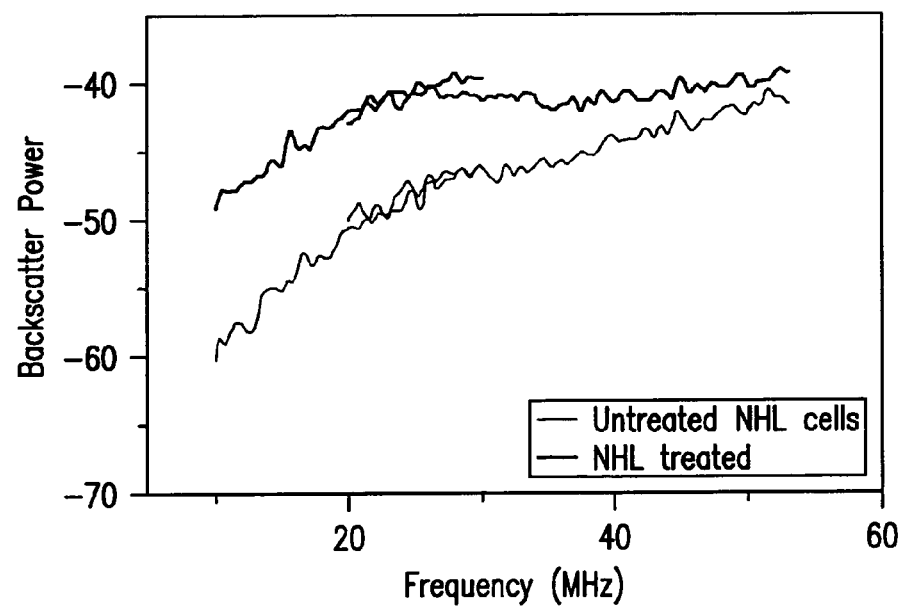
FIG.2C

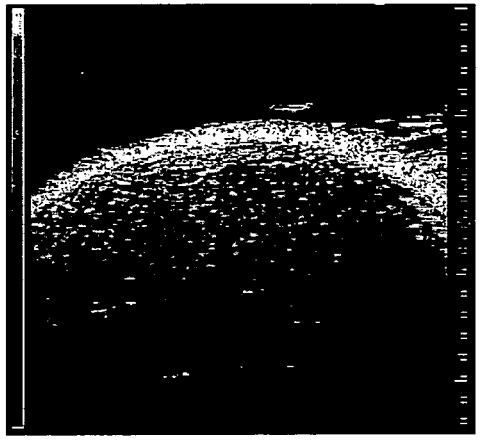
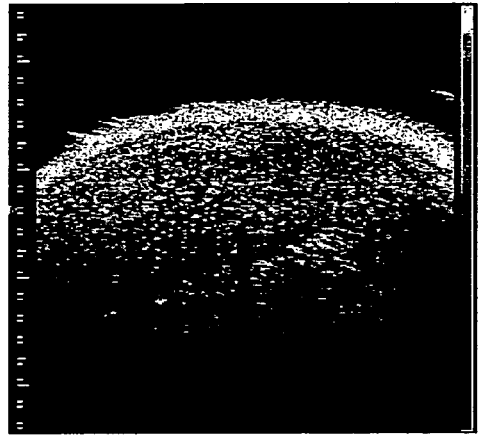
FIG.3A                FIG.3B
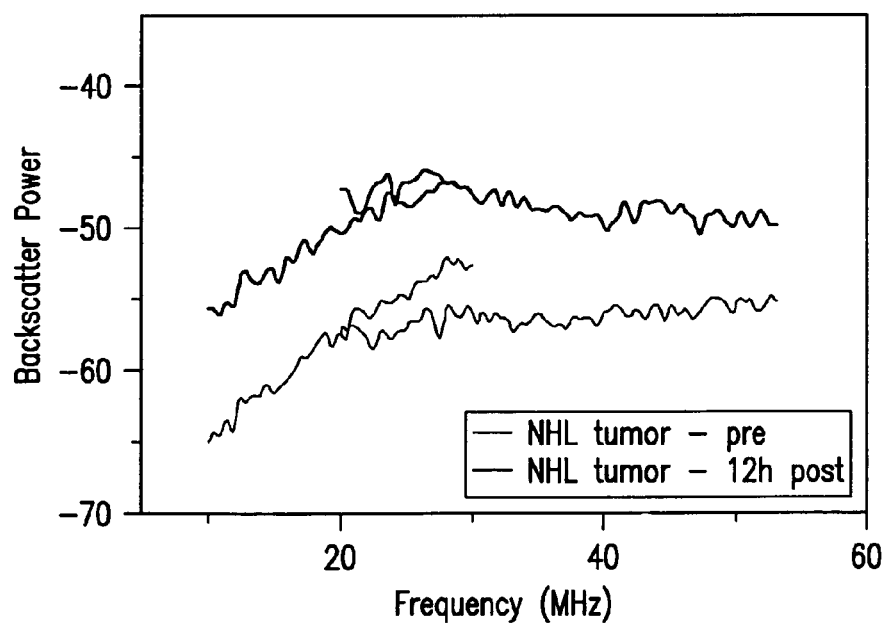
FIG.3C

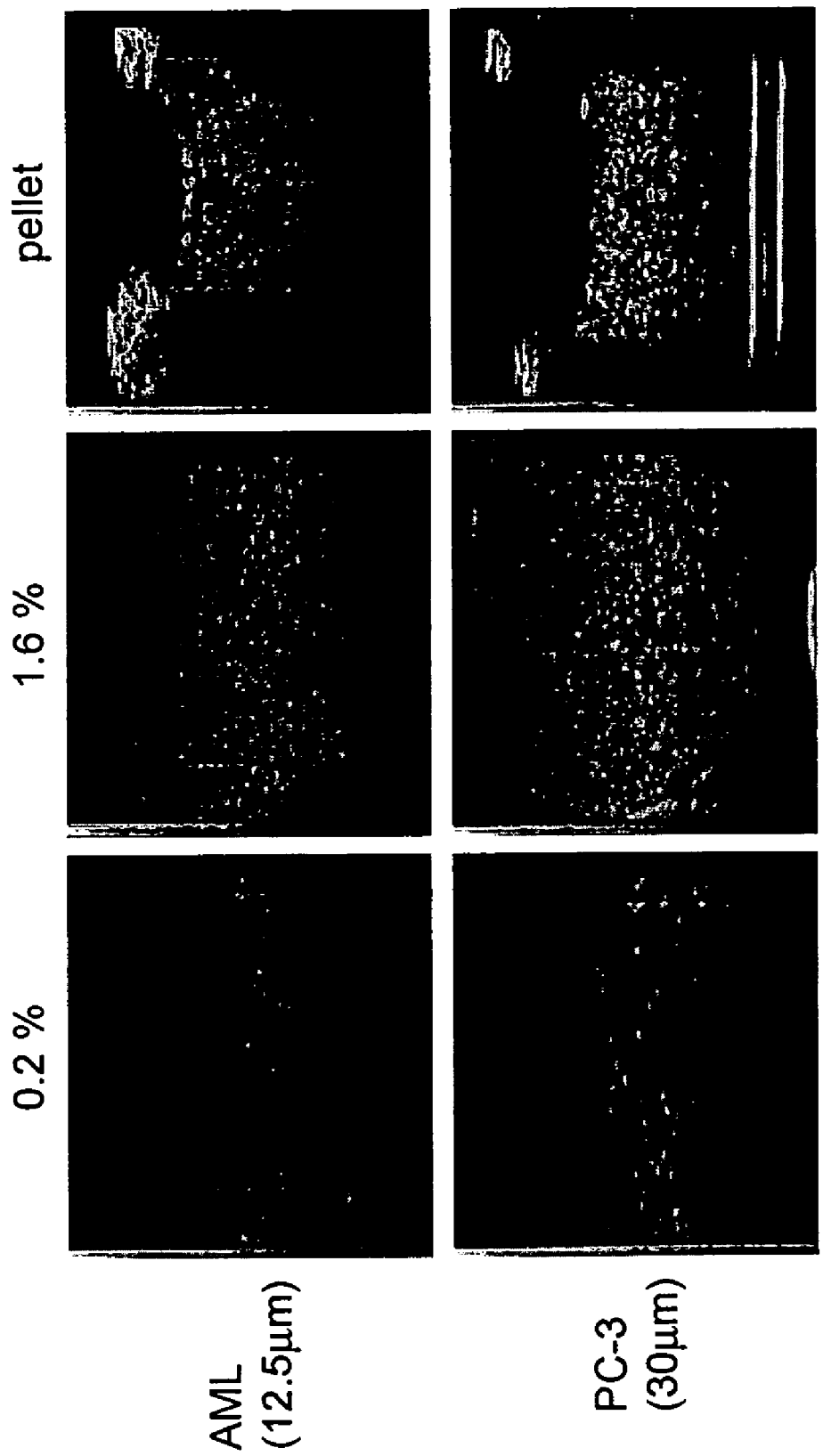

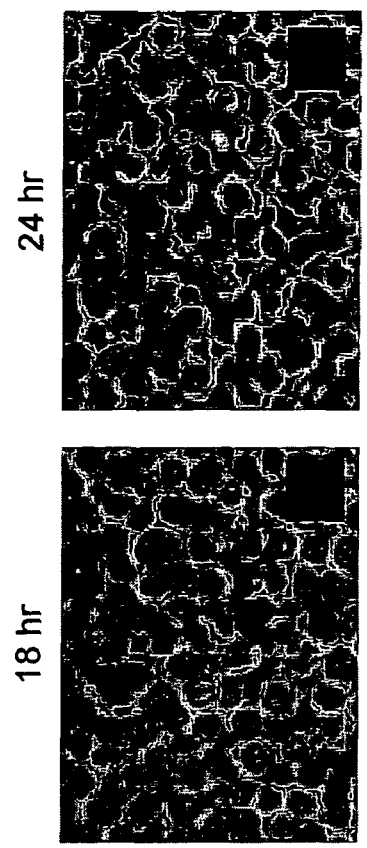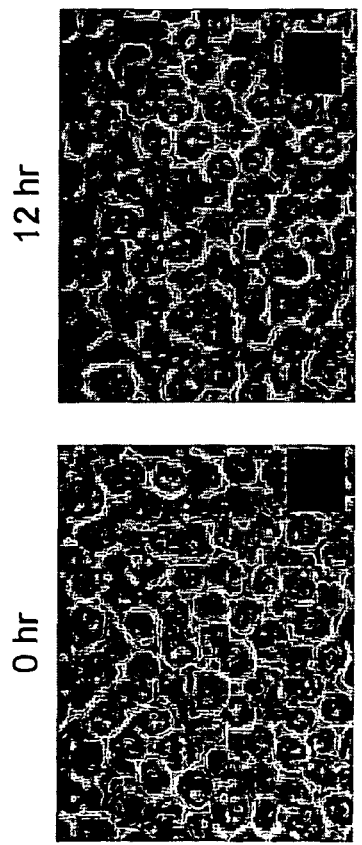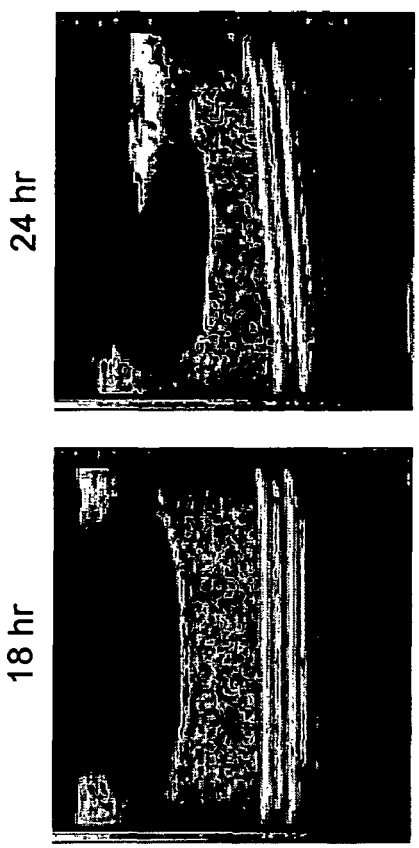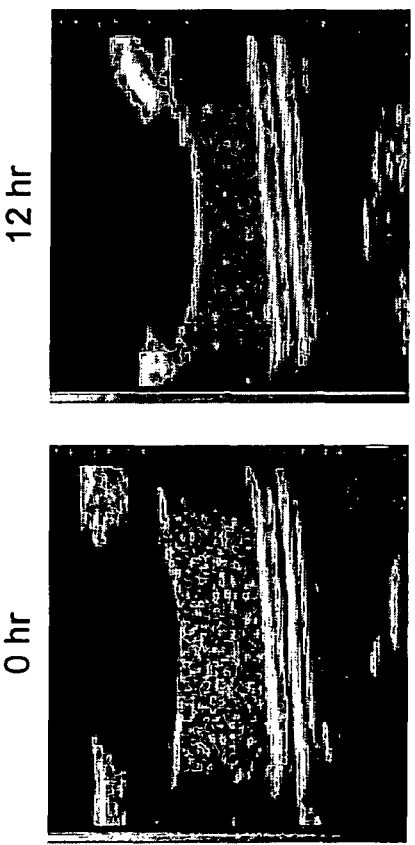

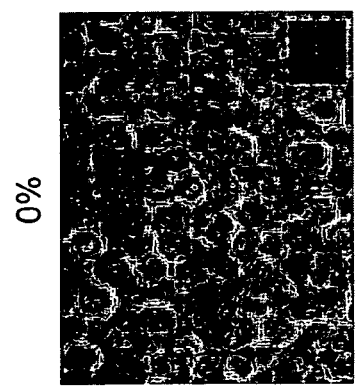
FIG.16A 0%
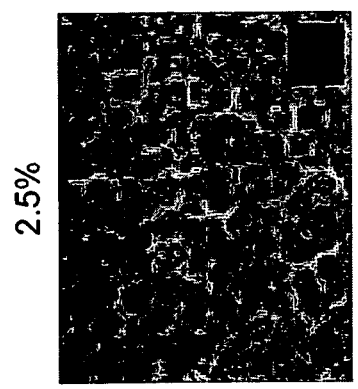
FIG.16B 2.5%
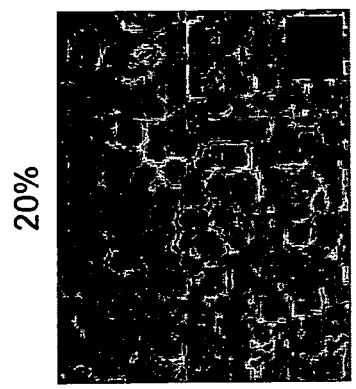
FIG.16C 20%
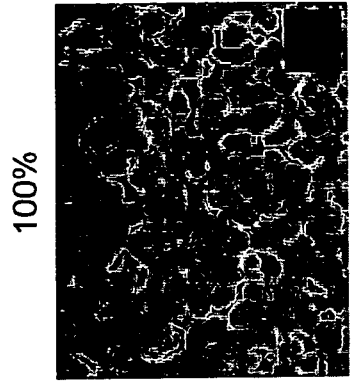
FIG.16D 100%
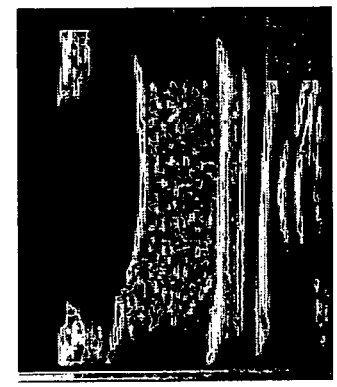
FIG.16E 0%
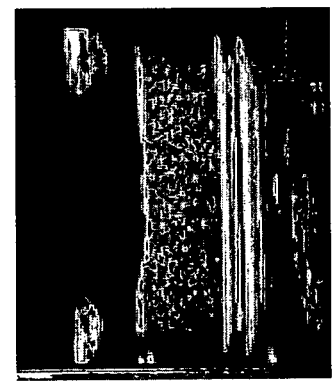
FIG.16F 2.5%
FIG.16G 20%
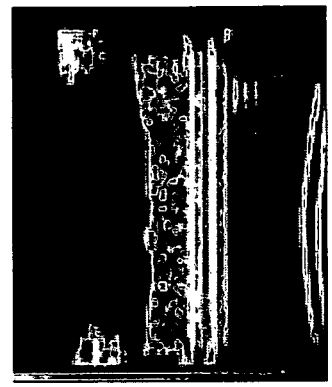
FIG.16H 100%

Pre Treatment 12 hours Post Treatment

Pre Treatment 12 hours Post Treatment

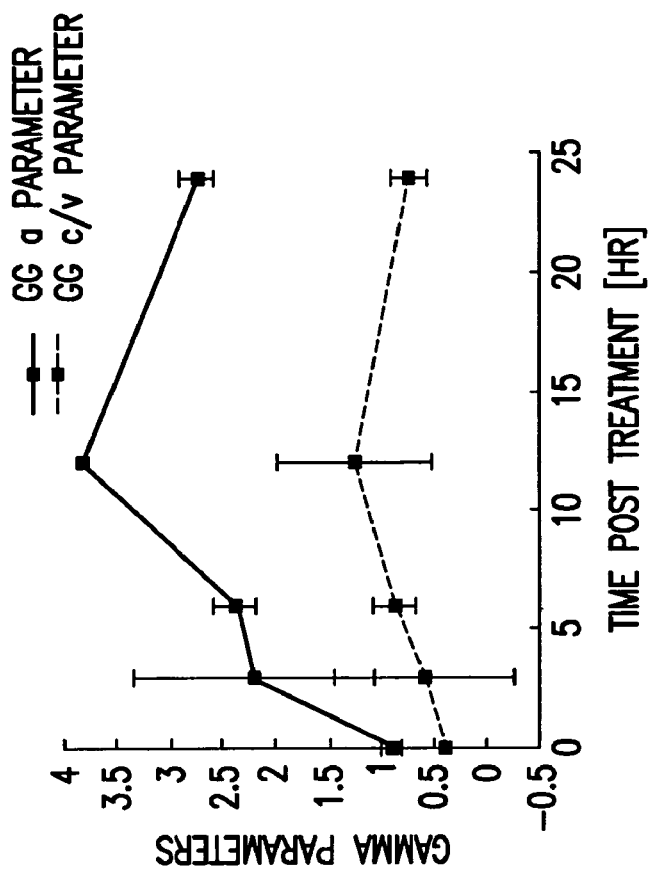

METHODS OF MONITORING CELLULAR DEATH USING LOW FREQUENCY ULTRASOUND

CROSS-REFERENCE TO RELATED APPLICATIONS

This application claims priority to U.S. Provisional Application No. 60/691,577, filed on Jun. 16, 2005. The aforementioned application is herein incorporated by reference in its entirety.

BACKGROUND OF THE INVENTION

It is useful in both experimental and clinical applications to know whether cells are undergoing cellular death. Cells can undergo death by apoptosis or non-apoptotic cell death. Cell death plays a significant role in both normal and disease-related biological processes. Cells undergo apoptosis in response to a variety of stresses including chemotherapy, radiation therapy, photodynamic therapy and heat. Whether a cell is undergoing apoptosis is currently determined by taking samples of cells or tissues of interest and observing, using histological and DNA measurement methods, whether the cells exhibit the morphological changes that are indicative of apoptosis. These changes include membrane blebbing, DNA condensation and DNA fragmentation. These methods, however, are not only invasive, but are also time-consuming, requiring processing of a cell or tissue sample before data relating to apoptosis can be obtained.

The ability to differentiate apoptotic cells or otherwise dead or dying cells from living cells non-invasively, in vitro, and in vivo at both superficial and deep sites, would potentiate clinical diagnoses and provide a more efficient way of studying apoptotic or non-apoptotic cell death and evaluating the clinical response of a subject to a therapeutic agent or regimen.

SUMMARY OF THE INVENTION

A method of detecting cellular damage within a subject can comprise transmitting low frequency ultrasound (20 MHz or below) into a selected site within the subject wherein the selected site has been exposed to a stress capable of causing cellular death at the selected site. At least a portion of ultrasound backscattered from the ultrasound transmitted into the selected site can be received. The received backscattered ultrasound can be compared to a control backscatter measurement. An increase or a decrease in intensity or spectral slope of the received backscattered ultrasound when compared to the control backscatter measurement can indicate cellular death and/or damage at the selected site within the subject. Also provided herein are systems for performing the disclosed methods.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several aspects of the invention and together with the description, serve to explain the principles of the invention.

FIG. 2 shows images of pellets of NHL cells, imaged using a 20 MHz ultrasound transducer, before treatment (A) and 16 hours after treatment using CHOP chemotherapy (B). The transducer focus in located about 1 mm below the pellet surface. (C) shows spectroscopic data collected with the 20 MHz (10-30 MHz band) and 40 MHz (20-56 MHz band) transducers, before treatment and 12 hours after CHOP chemotherapy.

FIG. 3 shows ultrasonic images (20 MHz transducer) of the NHL cells shown in FIG. 2 implanted in the hind leg of a mouse, forming a tumor. Images are of the same animal before treatment (A) and 12 hours after treatment (B). An increase in backscatter is observed. (C) shows spectroscopic data collected with the 20 MHz (10-30 MHz band) and 40 MHz (20-56 MHz band) transducers, before treatment and 12 hours after CHOP chemotherapy.

FIG. 7 shows B-scan images of the suspensions of various concentrations of AML cells (top row) and PC-3 cells (bottom row). At the lower concentrations individual cells are apparent, however as the concentration is increased the B-scan shows the speckle pattern characteristic of US images. While the AML pellet appears darker than the 1.6% concentration solution, the PC-3 pellet does not, indicating differences in the scattering interaction in solution vs. pellet.

FIG. 12 shows haematoxylin and eosin staining of pellets of AML cells treated for 0, 12, 18 and 24 hours with cisplatinum (A-D). B-scan images of the same pellets with a 20 MHz f#2.35 transducer (E-H). The pellet is the speckled region in the center, the hyperechoic line across the bottom is the plastic pellet container, the sides of the pellet container are visible in the top corners. The pellet shows a marked increase in intensity as the cells are treated for longer times.

FIG. 16 shows haematoxylin and eosin staining of pellets formed with mixtures of untreated and 0% (A), 2.5% (B), 20% (C) and 100% (D) cisplatinum treated AML cells (24 hour exposure). B-scan images of the same pellets with a 20 MHz f#2.35 transducer (E-H). The pellet is the speckled region in the center, the hyperechoic line across the bottom is the bottom of the plastic pellet container, the sides of the pellet container are visible in the top corners. There is a marked increase in intensity as the percentage of treated cells is increased, even between the pellets formed with 0% and 2.5% treated cells.

FIG. 22 shows Generalized Gamma PDF fitting parameters with 95% confidence intervals. Determined for the histograms shown in FIG. 21 for a single mouse imaged at times up to 48 hours post treatment.

DETAILED DESCRIPTION

Figure 1A:
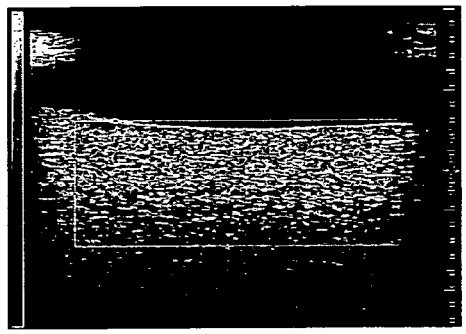
FIG. 1 shows results of exposure of HEP2 cells to the chemotherapeutic camptothesin. Pellets of unexposed cells imaged at 20 MHz (A) and 40 MHz (B) and camptothesin exposed cells (24 hour exposure) imaged at 20 MHz (C) and 40 MHz (D). Spectroscopic data (E) collected with the 20 MHz (10-30 MHz band) and 40 MHz (20-56 MHz band) transducers, before treatment and at a series of timepoints after treatment.
Figure 1B:
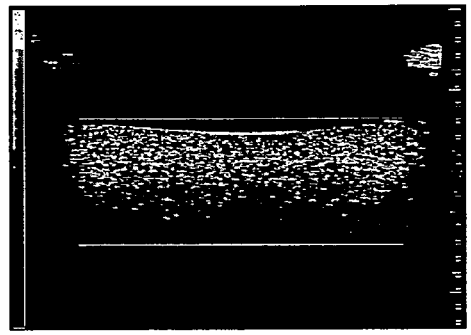
Figure 1C:
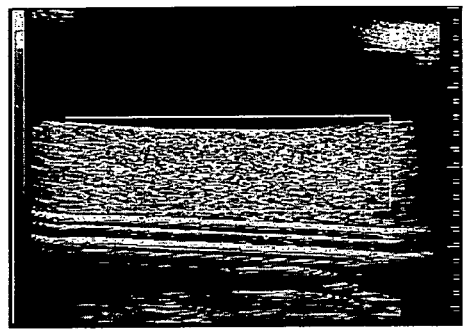
Figure 1D:
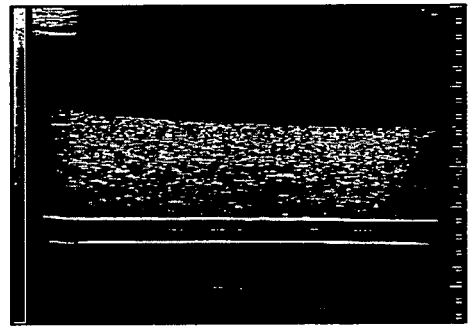
Figure 1E:
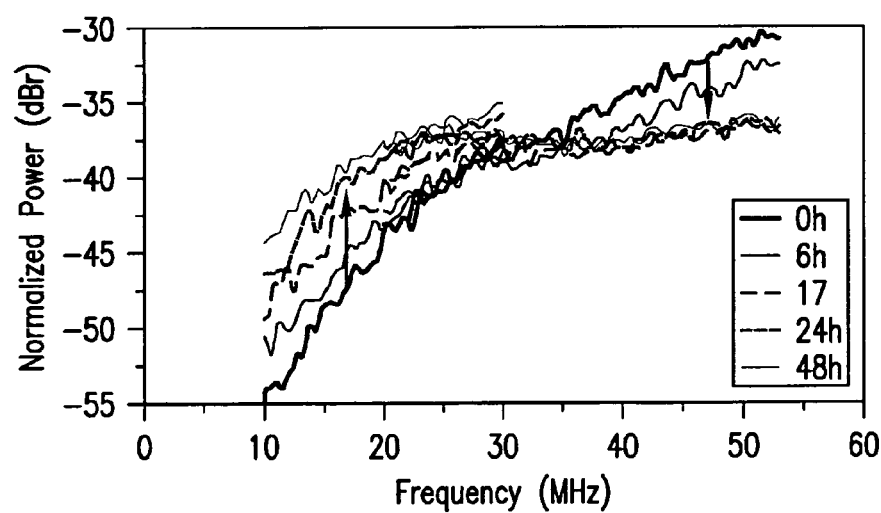

The present invention may be understood more readily by reference to the following detailed description and the Examples included therein and to the Figures and their previous and following description.

Before the present compounds, compositions, articles, devices, and/or methods are disclosed and described, it is to be understood that this invention is not limited to specific synthetic methods, specific components, or to particular therapeutic agents, as such may, of course, vary. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Thus, for example, reference to "an image" includes multiple images, reference to "a stress" or a "therapeutic agent" includes mixtures of two or more such stressors or agents, and the like.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not. For example, the phrase "optionally maintaining the therapeutic regimen" means that the therapeutic regimen may or may not be maintained and that the description includes both methods wherein the regimen is maintained and methods wherein the regimen is modified or altered.

As used throughout, by a "subject" is meant an individual. Thus, the "subject" can include domesticated animals, such as cats, dogs, etc., livestock (e.g., cattle, horses, pigs, sheep, goats, etc.), laboratory animals (e.g., mouse, rabbit, rat, guinea pig, etc.) and birds. In one aspect, the subject is a mammal such as a primate or a human.

Provided herein are methods of using low frequency ultrasound imaging to monitor and/or detect the process of cellular death and/or damage. Any process leading to cellular death can be detected or monitored including, for example, death by apoptosis, necrosis, oncosis, apoptotic necrosis and apoptotic oncosis. The process of cellular death can be detected or monitored by identifying or detecting one or more dead cell, dying cell, damaged cell or a combination thereof. When the term "cellular death" is used herein, it includes both a dead cell and a cell undergoing a cellular death process, i.e. a dying cell. Dead or dying cells can be monitored or detected by detecting cellular damage of the cell.

Cellular death can be monitored in vitro or in vivo using the disclosed methods. Although it has been possible to differentiate non-invasively between dying and viable cell populations based on changes in integrated backscatter at high frequency, the limited penetration depth of high frequency ultrasound restricts its use to superficial sites. Moreover, as is shown in FIG. 1, the increase in backscatter can be frequency dependent, much weaker at higher frequencies, and thus non-detectable, compared to frequencies equal to or lesser than 20 MHz.

The disclosed methods can be used to monitor cellular death at deep or superficial sites within a subject with low frequency ultrasound. Monitoring of cellular death at deep and superficial sites allows for analysis and potential modification of a therapeutic regimen being administered to a subject afflicted with a superficial or deep neoplastic or other disease condition.

Thus, provided herein are methods of monitoring and/or detecting cellular death within a subject comprising transmitting low frequency ultrasound into a selected site within the subject wherein the selected site has been exposed to a stress capable of causing cellular death at the selected site. As stated above, the use of "cellular death" herein includes the process of cellular death. The process of cellular death can comprise damage to one or more cell and eventual death of that cell. Thus, as referred to herein, methods of monitoring cellular death can be accomplished by detecting cellular damage. A method of detecting cellular damage can include identifying a damaged, dying or a dead cell. Also, as used herein, the term "monitor" can be used interchangeably with "detect." Thus, "monitoring" cellular death can be accomplished by detecting a dead or damaged cell.

One example of a process of cellular death that can be monitored or detected using the disclosed methods is apoptosis. Other exemplary processes leading to death that can be monitored include death by necrosis, oncosis, apoptotic necrosis and apoptotic oncosis.

"Apoptosis-inducing stress," "stress capable of causing cellular death," or "stressor," as referred to herein, is meant to encompass any stress which will result in the initiation of apoptosis or cellular death. Examples of such stresses include, but are not limited to, chemotherapeutic agents, drugs, photodynamic therapy, thermal therapy, cryotherapy, chemical modifiers aimed at protecting tissues from radiations such as sunscreens, radiations including X-rays, gamma rays and ultraviolet radiations, oxygen and/or nutrient deprivation that can occur after organ removal for transplantation for example, and the activation of genes that can initiate an apoptotic response as well as aging and developmental processes. Accordingly, the term "apoptosis-inducing stress" or "stress capable of causing cellular death" is also meant to encompass biological events that occur normally in tissues to induce apoptosis or cellular death. Cellular death or damage caused by necrosis can also be monitored or detected.

Cellular damage can be detected within a subject. A method of detecting cellular damage comprises transmitting ultrasound having a frequency of 20 megahertz (MHz) or below into a selected site within the subject, wherein the selected site has been exposed to a stress capable of causing cellular damage. The method can comprise receiving data backscattered from the selected site and comparing the received backscattered data to control data to detect cellular damage within the subject. A modulation of the received backscattered data from the selected site compared to the control data can indicate cellular damage within the subject. The cellular damage detected can be one or more dying or dead cell or a combination thereof. The one or more dying cell can be undergoing apoptosis or necrosis. If the detected cell is dead, its cause of death can be apoptosis or necrosis. Other death processes that can be detected by detecting cellular damage include oncosis, apoptotic necrosis and apoptotic oncosis.

Ultrasound having a frequency of 20 megahertz (MHz) or below can be transmitted into a selected site within the subject after the selected site has been exposed to a stress capable of causing cellular damage at the selected site. Exemplary stressors capable of causing cellular damage are described herein and are also referred to as stressors capable of causing cellular death.

In some examples, a modulation in ultrasound backscatter in a formed ultrasonic image or scan can be compared to a control image or scan. When compared to the control image, an increase in backscatter represented in a scan or image can indicate the detection of cellular damage at the selected site within the subject. For example, an increase in the ultrasound backscatter, brightness, or intensity in the formed image as compared to an intensity measurement of backscatter or brightness of a control image can indicate the detection of cellular damage at the selected site within the subject. A decrease in ultrasound backscatter or brightness in a formed image when compared to the ultrasound backscatter or brightness of a control image can also indicate cellular damage at a selected site within the subject.

For example, a decrease in the ultrasound backscatter, brightness, or intensity in a formed image as compared to an intensity measurement of backscatter of the control image can indicate the detection of cellular damage at the selected site within the subject. Thus, a selected site within a subject can be imaged using ultrasound having a frequency of 20 megahertz (MHz) or below to obtain a first image. The selected site can then be exposed to a stress capable of inducing cell damage. The selected site or a portion thereof, can be imaged at one or more subsequent time using ultrasound having a frequency of 20 MHz to obtain at least a second image. The brightness, intensity, and/or backscatter can be compared between the pre-stress image and one or more post-stress image to detect cellular death, wherein a modulation of second image as compared to the first image indicates cellular damage at the selected site within the subject.

A signal amplitude of a region of interest of the selected site in the first and second images can also be determined and compared, wherein a modulation of second image signal amplitude as compared to the first image signal amplitude indicates cellular damage at the selected site within the subject. For example, the second image region can exhibit an increase or a decrease in amplitude to indicate the detection of cellular damage. A modulation of the frequency spectrum between one or more images can also be determined. For example, a slope of an average of the normalized frequency spectrum can be increased or decreased, which can indicate the detection of cellular damage.

As used herein, low frequency ultrasound refers to ultrasound transmitted at a frequency of 20 MHz or lower. Similarly, "low frequency ultrasound imaging" is meant to refer to ultrasound imaging at frequencies of 20 MHz or lower. Thus, ultrasound can be transmitted, or imaging can be performed, at 20 MHz, or at, about or between, 19 MHz, 18 MHz, 17 MHz, 16 MHz, 15 MHz, 14 MHz, 13 MHz, 12 MHz, 11 MHz, 10 MHz, 9 MHz, 8 MHz, 7 MHz, 6 MHz, 5 MHz, 4 MHz, 3 MHz, 2 MHz, 1 MHz, or lower. For example, an ultrasound transducer with a center frequency of 20 MHz can be used such as the VisualSonics Inc. (Toronto, CA) VS-40B model ultrasound transducer and/or system, with imaging or transmission of ultrasound being performed at the center frequency of 20 MHz or at lower frequencies within the operating bandwidth of the transducer. Other transducers of a variety of center frequencies can also be used. Thus, transducers can be used that have a center frequency and/or a portion of their operating bandwidth at 20 MHz or below.

The low frequency ultrasound transmitted into the selected site, or a portion thereof, can be backscattered. At least a portion of ultrasound backscattered from the ultrasound transmitted into the selected site can be received. The ultrasound can be transmitted and received using the same transducer and/or ultrasound probe as would be clear to one skilled in the art. The received backscattered ultrasound can be compared to a control backscatter measurement. Optionally, an increase in the received backscattered ultrasound when compared to the control backscatter measurement indicates cellular death and/or damage indicating a dead or dying cell at the selected site within the subject. Optionally, the increase in the received backscattered ultrasound is represented by an increase in an intensity measurement of the received backscattered ultrasound when compared to an intensity measurement of the control backscatter measurement indicating cellular death at the selected site within the subject.

The "control backscatter measurement," "control image," or "control" as used herein can comprise a low frequency ultrasound image or images, or a backscatter data measurement, including spectral data, taken from the cells or tissues of interest prior to the application of a stress capable of causing cellular death or damage or at any time prior to the acquisition of non-control data or images. A control image or data can be acquired from the same or a different subject as the non-control measurement. Thus, a control can comprise any backscatter data, however processed, including an image or spectral data, or representations thereof, obtained prior to exposure to a stress capable of causing cellular death or damage. A control can also comprise backscatter data, however processed, including an image or spectral data, or representations thereof, obtained after exposure to a stress capable of causing cellular death or damage. In this case, the control data can be obtained prior to the non-control data relative to the exposure to the stress.

A control measurement can be obtained either in-vivo or ex-vivo. Such data or an image can be referred to herein as a "before image." The taking of a low frequency ultrasound image following application of the stress, can be referred to herein as an "after image."

Alternatively, low frequency ultrasound images or backscatter measurements of treated and untreated regions of the sample or tissue can simultaneously be taken. In this case, the ultrasound image or measurement of the untreated region can be used as the control. If such an image is used, it is equivalent to the "before image" and the ultrasound image of the treated region would be equivalent to the "after image."

Moreover, other controls can be used. For example, any similar tissue or cell that has not been exposed to the stress capable of causing cellular death can be used as a control by taking an image or measurement from the cell or tissue. Furthermore, in the methods described herein, measurements can be compared to a standard based on tissues or cells not exposed to the stress capable of causing cellular death. Thus, an increase in signal intensity that can be used to indicate apoptosis or cellular death in a particular biological system can be determined by correlating the change in signal intensity with a standard assay for apoptosis or cellular death such as fluorescent staining of DNA when the biological system can be exposed to a known apoptosis-inducing or cellular death inducing stress.

Further provided herein is a method of monitoring cellular death within a subject comprising transmitting low frequency ultrasound into a selected site within the subject, wherein the selected site has been exposed to a stress capable of causing cellular death at the selected site. At least a portion of ultrasound backscattered from the ultrasound transmitted into the selected site can be received. A spectral slope of the received backscattered ultrasound can be compared to a spectral slope from a control backscatter measurement, wherein a modulation in the received backscattered ultrasound spectral slope when compared to the spectral slope of the control backscatter measurement indicates cellular death at the selected site within the subject. Optionally, an increase in the spectral slope of the received backscattered ultrasound when compared to the spectral slope of the control backscatter measurement indicates cellular death at the selected site within the subject. Optionally, a decrease in the spectral slope of the received backscattered ultrasound when compared to the spectral slope of the control backscatter measurement indicates cellular death at the selected site within the subject.

Also provided herein is a method of monitoring cellular death within a subject comprising transmitting low frequency ultrasound into a selected site within the subject wherein the selected site has been exposed to a stress capable of causing cellular death at the selected site. At least a portion of ultrasound backscattered from the ultrasound transmitted into the selected site can be received. The received backscattered ultrasound can be compared to a control backscatter measurement. A decrease in the received backscattered ultrasound when compared to the control backscatter measurement indicates cellular death at the selected site within the subject. Optionally, the decrease in the received backscattered ultrasound is represented by a decrease in an intensity measurement of the received backscattered ultrasound when compared to an intensity measurement of the control backscatter measurement indicating cellular death at the selected site within the subject.

Thus, apoptosis or cellular death can be indicated in the sample or region of tissue if either or both the signal intensity increases and/or the slope of the frequency spectrum increases (spectral slope). The zero megahertz intercept can also be used to monitor cellular death. For example, the process of cellular death can be monitored by detecting cellular damage wherein a modulation of zero slope intercept between a control and a sample or non-control measurement. An increase or a decrease in the zero megahertz intercept can indicate cellular damage.

Apoptosis or cellular death can also be indicated in a sample or region of tissue if either or both the signal intensity decreases and/or the slope of the frequency spectrum decreases (spectral slope). The regions of tissue that satisfy these criteria can be color coded on the original ultrasound image, for example. There are various methods known in the art for calculating the signal amplitude, slopes of the frequency spectra (spectral slope) and the average scatterer size parameters, and any of these can be used, with the choice being one that a person skilled in the art can select readily. The methods can be used to detect and monitor cellular death in cells or tissues, in vitro, in vivo or ex vivo using low frequency ultrasound imaging.

Further provided herein is a method of monitoring cellular death within a subject comprising transmitting low frequency ultrasound into a selected site within the subject wherein the selected site has been exposed to a stress capable of causing cellular death at the selected site. At least a portion of ultrasound backscattered from the ultrasound transmitted into the selected site can be received. At least a portion of the received backscattered ultrasound can be processed to form an image. The formed image can be compared to a control image, wherein an increase in ultrasound backscatter of the formed image when compared to the control image can indicate cellular death at the selected site within the subject. Optionally, the increase in the ultrasound backscatter of the formed image is an increase in intensity of backscatter of the formed image when compared to an intensity measurement of backscatter of the control image indicating cellular death at the selected site within the subject. The formed image can also be compared to a control image, wherein a decrease in ultrasound backscatter of the formed image when compared to the ultrasound backscatter of the control image indicates cellular death at the selected site within the subject. Optionally, the decrease in the ultrasound backscatter of the formed image is represented by a decrease in intensity of backscatter of the formed image when compared to an intensity measurement of backscatter of the control image indicating cellular death at the selected site within the subject.

Also provided herein is a method of monitoring cellular death within a subject, comprising imaging a selected site within the subject using low frequency ultrasound imaging to obtain a first image. The selected site can then be exposed to a stress capable of inducing cell death. The selected site or a portion thereof can be imaged, using low frequency ultrasound imaging at subsequent timed intervals to obtain at least a second image. A signal amplitude of a region of interest can be measured of the selected site in the first and second images. The signal amplitude measurements can be compared for the regions of interest in the first and second images and it can be determined whether the second image region exhibits an increase in amplitude that can indicate that cellular death has occurred or is occurring. The signal amplitude measurements can also be compared for the regions of interest in the first and second images and a determination can be made whether the second image region exhibits a decrease in amplitude indicating that cellular death has occurred or is occurring. Optionally, the method can comprise measuring a change in a frequency spectrum of an ultrasound backscatter signal in the region of interest between the first and second images and confirming that cellular death has occurred or is occurring when a slope of an average of the normalized frequency spectrum has increased. If a decrease is determined, optionally the method can comprise measuring a change in a frequency spectrum of an ultrasound backscatter signal in the region of interest between the first and second images and confirming that cellular death has occurred when a slope of an average of the normalized frequency spectrum has decreased.

The methods described herein can involve either obtaining the radiofrequency signal and measuring the amplitude, which can be the square root of intensity, averaged over a region of interest or if radiofrequency data is not available from the ultrasound machine, using a calibration curve from the ultrasound machine manufacturer to convert the final machine signal into an average radiofrequency amplitude over the region of interest. In either case, the signal amplitude can be measured over the region exposed to the stress and over control untreated regions at any timepoint after the stress can be applied.

Optionally, a region of apoptosis or cellular death, as a result of the treatment of the tissues/cells, is indicated where the signal amplitude rises by a significant factor, for example, where the signal amplitude rises by at least a factor of one, two, three, four or more times.

The threshold of the increase in signal intensity that can be used to indicate apoptosis or cellular death in a particular biological system can be determined by correlating the change in signal intensity with a standard assay for apoptosis or cellular death such as fluorescent staining of DNA when the biological system is exposed to a known apoptosis-inducing or cellular death inducing stress. A graph of the change in ultrasound signal intensity versus the percentage of apoptotic cells as measured using the standard apoptosis assay can then be used to determine the percentage of apoptotic cells in that biological system to any apoptosis-inducing stress using low frequency ultrasound imaging.

Subsequent to analyzing signal amplitude data, a frequency analysis can be performed on the radiofrequency ultrasound signals. This can involve taking a Fourier transform of the data from both treated and untreated regions. For example, 20 A-scan lines of radiofrequency data and preferably 20-50 lines can be acquired from each region of interest and can be digitized by an ultrasound scanner. The window length over which the A-scan radiofrequency signal is digitized and can correspond to between about 0.5 and 3 mm in the image. The window length can be at the lower end of this range to reduce the effects of ultrasound attenuation in the frequency analysis.

Fourier transforms of the acquired radiofrequency A-scan lines are calculated and then squared to give the Fourier power spectrum for each A-scan. The Fourier power spectrum can then be normalized against a reference Fourier power spectrum of the ultrasound pulse from the transducer. This can be achieved by dividing the Fourier power spectrum of the signals from the region of interest by the Fourier power spectrum of the ultrasound reflected from a hard surface, such as a quartz flat.

The normalized power spectra can be calculated between bandwidth limits where the value of the reference Fourier power spectrum can be −15 dB or 3% of the maximum value at the center frequency of the ultrasound imaging system. Linear regression can be performed on the normalized power spectrum from each A-scan line. The linear regression lines fitted to each normalized Fourier power spectrum can then be averaged over all the scan lines acquired from a region of interest to give an average fitted normalized Fourier power. The average fitted normalized Fourier power spectra can be plotted as graphs of $10 \log_{10}$ (normalized power) versus frequency. The slope of this line with function $y=mx+c$, is m. Apoptosis or cellular death can be indicated by the slope of the average fitted normalized Fourier power spectrum versus frequency becoming significantly more positive during treatment.

The method of frequency analysis described herein is well described in the literature and can be implemented readily by a person skilled in the art. The threshold of the increase in slope of the average fitted normalized Fourier power spectrum that can be used in any particular biological system to indicate apoptosis can be determined by first correlating the increase in slope with a standard assay of apoptosis or cellular death when a known apoptosis inducing agent or cellular death causing stress is applied to that biological system. A graph of the change in slope of the average fitted normalized Fourier power spectrum versus percentage of apoptotic cells and/or dying cells as measured using the standard assay can then be the calibration curve used to determine the percentage of apoptotic/dying cells in that biological system due to any stress capable of causing cell death using low frequency ultrasound imaging.

Other methods in addition to Fourier analysis can be used to measure the change in the radiofrequency ultrasound signals due to apoptosis and/or cell death reflected back from the tissue or cells for example the increase or decrease in ultrasound signal can be measured by calculating the mid-band fit of the average normalized Fourier power spectrum. The "mid-band fit" as referred to herein can be defined as the value of the average normalized Fourier power spectrum at the center frequency of the chosen bandwidth. Similarly, the change in the frequency content of the ultrasound signals due to apoptosis/cell death can be measured by performing wavelet analysis, for example.

To further confirm the occurrence of apoptosis or cellular death, the average scatterer size can be calculated from the radiofrequency spectra. This determination is not independent of slope calculated as set out above, and thus functions to verify apoptosis. Several methods have been published for calculating scatterer size from ultrasound backscatter signals including those of Lizzi, et al (Theoretical framework for spectrum analysis in ultrasonic tissue characterization, Journal of the Acoustical Society of America 1983, 73, 1366-1373) and by Hall et al (Describing small-scale structure in random media using pulse echo ultrasound Journal of the Acoustical Society of America 1990, 87, 179-192; Parametric ultrasound imaging from backscatter coefficient measurements: Image formation and interpretation Ultrasonic Imaging 1990, 12, 245-267). Apoptosis and/or cell death can be confirmed by a significant decrease in the average scatterer size in the region of interest.

The threshold in decrease in scatterer size that can be used to indicate apoptosis/or cell death in any particular biological system can be determined by correlating the decrease in scatterer size calculated from the radiofrequency ultrasound data with the percentage of cells undergoing apoptosis/cell death as measured using a standard assay when a known apoptosis-inducing inducing agent is applied to that biological system. A graph of the decrease in scatterer size calculated from the ultrasound imaging radiofrequency data decrease versus percentage of apoptotic cells as measured using a standard assay can be used as a calibration curve to determine the percentage of apoptotic cells in that biological system due to any apoptosis-inducing stress using low frequency ultrasound imaging.

One or more ultrasound image (B-Scan or C-Scan) of the cells or tissues of interest can be taken before the apoptosis inducing treatment is applied. Optionally, a second set of images of the same area during and/or after treatment can be taken. The signal level change in the region of interest can be calculated. This calculation can be achieved by using a calibration curve from the ultrasound machine manufacturer to convert the final machine signal (pixel level) into an average radiofrequency signal power over the region of interest or, if the radiofrequency signal can be obtained from the machine, it can be used to calculate an average signal power over the region of interest. The signal amplitude can be measured over a region of interest within the region of tissue exposed to the treatment, at any timepoint of interest after the treatment is applied and compared to the same region of interest in the images before the treatment was applied or compared to a neighboring area of untreated tissue. In addition, the percentage of apoptotic cells or dying or dead cells in any biological system can be determined by using a calibration curve as set out above. A frequency analysis on the radiofrequency data can also be performed. Optionally, the change in the slope of the average normalized Fourier power spectrum can be calculated as set out above.

Another calculation can be performed to confirm that the cause of changes in signal amplitude and frequency spectra slope is indeed apoptosis. This calculation derives the average scatterer size from the frequency spectra data. One method of calculating the average scatterer size can be to employ the method of Lizzi et al. (supra).

In addition, the percentage of apoptotic cells in particular biological systems can be determined using a calibration curve for each biological system as set out above. Data from the calculations above can be presented in several ways. Results of each of the individual calculations can be displayed and stored as a numeric value on the ultrasound imaging machine together with an indication as to whether they are consistent with apoptosis or cellular death when compared to the threshold values set out above. Similarly, the percentage of apoptotic cells or dead or dying cells can be displayed and stored. Increases or decreased in both signal intensity and slope of the average normalized Fourier power spectrum over the thresholds can be used to report a positive finding that apoptosis is occurring in the sample as a result of the stress capable of causing cellular death.

Provided herein is a method of monitoring cellular death within a subject comprising transmitting low frequency ultrasound into a selected site within the subject, wherein the selected site has been exposed to a stress capable of causing cellular death at the selected site. At least a portion of ultrasound backscattered from the ultrasound transmitted into the selected site can be received and a statistic of the envelope of the received backscattered ultrasound can be determined. The determined statistic can be compared to a control, wherein an increase or a decrease of the determined signal statistic when compared to a corresponding signal statistic of the control indicates cellular death at the selected site within the subject.

Further provided herein is a method of monitoring cellular death within a subject, comprising imaging a selected site within the subject using low frequency ultrasound imaging to obtain a first image and exposing the selected site to a stress capable of causing cellular death. The method can comprise imaging the selected site or a portion thereof, using low frequency ultrasound imaging at subsequent timed intervals to obtain at least a second image and determining a statistic of the envelop of a backscatter signal from a region of interest of the selected site in the first and second images. The envelop statistic from the regions of interest in the first and second images can be compared and it can be determined whether the second image region exhibits an increase or a decrease in the envelope statistic indicating that cellular death has occurred.

The disclosed methods have many potential applications. These include but are not restricted to human and veterinary, diagnostic and therapeutic applications. Such applications include, but are not limited to, the testing of drugs and other chemical compounds for toxicity or therapeutic effect mediated by apoptosis, the study of the effects of oncogenes and other genes on apoptosis and the measurement of the viability of organs and tissues for transplantation.

The disclosed methods can be used and studied in cells in vitro, in human and animal tissues ex vivo and in vivo and for specific clinical applications including the monitoring of patient responses to therapies including chemotherapy, radiation therapy, photodynamic therapy, gene therapy and any other therapy that can involve the triggering of an apoptotic, necrotic, or other cellular damage or death response in cells. An exemplary application can be to monitor apoptosis in inflammatory tissues after triggering of the immune system, which is a potential treatment for immune disorders. Further applications include studying the effects of ultraviolet, X-ray and gamma radiation on cells and tissues as well as chemical modifiers such as sunscreens aimed at protecting tissues from these radiations. Moreover, radiation and chemotherapy treatment regimens can be monitored.

Provided herein is a method of monitoring a therapeutic regimen within a subject, comprising administering to the subject a therapeutic agent capable of causing cellular death at a selected site within the subject. Low frequency ultrasound can be transmitted into the selected site within the subject. At least a portion of ultrasound backscattered can be received from the ultrasound transmitted into the selected site. The received backscattered ultrasound can be compared to a control backscatter measurement, wherein an increase in the received backscattered ultrasound when compared to the control backscatter measurement indicates cellular death at the selected site within the subject. Optionally, the increase in the received backscattered ultrasound can be an increase in an intensity measurement of the received backscattered ultrasound when compared to the intensity of the control backscatter measurement indicating cellular death at the selected site within the subject. Optionally, the method can comprise determining whether the therapeutic regimen has been effective based on the compared backscattered ultrasound. For example, an increase in the intensity of backscattered ultrasound when compared to the control indicates an effective treatment regimen. If it is determined that the treatment regimen is effective, administration of the effective therapeutic regimen to the subject can be optionally maintained.

Further provided herein is a method of monitoring a therapeutic regimen within a subject comprising administering to the subject a therapeutic agent capable of causing cellular death at a selected site within the subject. Low frequency ultrasound can be transmitted into the selected site within the subject. At least a portion of ultrasound backscattered from the ultrasound transmitted into the selected site can be received. A spectral slope of the received backscattered ultrasound can be compared to a control spectral slope backscatter measurement. A modulation in the spectral slope of the received backscattered ultrasound when compared to the control spectral slope backscatter measurement can indicate cellular death at the selected site within the subject.

Optionally, an increase in the spectral slope of the received backscattered ultrasound when compared to the spectral slope of the control backscatter measurement can indicate cellular death at the selected site within the subject.

Optionally, a decrease in the spectral slope of the received backscattered ultrasound when compared to the spectral slope of the control backscatter measurement can indicate cellular death at the selected site within the subject. It can be further determined whether the treatment regimen is effective based on the compared backscattered ultrasound wherein an increase in the spectral slope of the backscattered ultrasound when compared to the control indicates an effective treatment regimen. It can also be determined that the therapeutic regimen has been effective based on the compared backscattered ultrasound wherein a decrease in the spectral slope of the backscattered ultrasound when compared to the control indicates an effective treatment regimen. If it is determined that the treatment regimen is effective, the effective therapeutic regimen can be optionally maintained. Moreover, it can be determined that the therapeutic regimen has not been effective based on the compared backscattered ultrasound. Optionally, no change or a decrease in backscattered ultrasound when compared to the control indicates a non-effective treatment regimen. If it is determined that the therapeutic regimen has not been effective the regimen can be optionally changed or modified.

Provided herein is a method of monitoring a therapeutic regimen within a subject, comprising administering to the subject a therapeutic agent capable of causing cellular death at a selected site within the subject. Low frequency ultrasound can be transmitted into the selected site within the subject. At least a portion of ultrasound backscattered can be received from the ultrasound transmitted into the selected site. The received backscattered ultrasound can be compared to a control backscatter measurement, wherein a decrease in the received backscattered ultrasound when compared to the control backscatter measurement indicates cellular death at the selected site within the subject. Optionally, the decrease in the received backscattered ultrasound can be evaluated by a decrease in an intensity measurement of the received backscattered ultrasound when compared to the intensity of the control backscatter measurement indicating cellular death at the selected site within the subject. Optionally, the method can comprise determining whether the therapeutic regimen has been effective based on the compared backscattered ultrasound. Optionally, a decrease in the intensity of backscattered ultrasound when compared to the control indicates an effective treatment regimen. If it is determined that the treatment regimen is effective, the method optionally can comprise maintaining administration of the effective therapeutic regimen to the subject. Further provided herein is a method of monitoring a therapeutic regimen using signal statistics or parameters as described above.

The disclosed methods can be used to monitor a therapeutic regimen administered to a subject with a neoplastic condition. The neoplastic condition can be superficial or deep within the subject. The neoplastic condition can be selected from the group consisting of lymphomas (Hodgkins and non-Hodgkins), B cell lymphoma, T cell lymphoma, myeloid leukemia, leukemias, mycosis fungoides, carcinomas, carcinomas of solid tissues, squamous cell carcinomas, adenocarcinomas, sarcomas, gliomas, blastomas, neuroblastomas, plasmacytomas, histiocytomas, melanomas, adenomas, hypoxic tumors, myelomas, AIDS-related lymphomas or sarcomas, metastatic cancers, bladder cancer, brain cancer, nervous system cancer, squamous cell carcinoma of head and neck, neuroblastoma/glioblastoma, ovarian cancer, skin cancer, liver cancer, melanoma, squamous cell carcinomas of the mouth, throat, larynx, and lung, colon cancer, cervical cancer, cervical carcinoma, breast cancer, epithelial cancer, renal cancer, genitourinary cancer, pulmonary cancer, esophageal carcinoma, head and neck carcinoma, hematopoietic cancers, testicular cancer, colo-rectal cancers, prostatic cancer, or pancreatic cancer.

Other diseases associated with increased apoptosis that can be monitored using the disclosed methods, include, but are not limited to AIDS, neurodegenerative disorders (such as Alzheimer's disease, Parkinson's disease, Amyotrophic lateral sclerosis, Retinitis pigmentosa, Cerebellar degeneration and brain tumor or prior associated disease), autoimmune disorders (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) myelodysplastic syndromes (such as aplastic anemia), graft v. host disease, ischemic injury (such as that caused by myocardial infarction, stroke and reperfusion injury), liver injury (e.g., hepatitis related liver injury, ischemia/reperfusion injury, cholestosis (bile duct injury and liver cancer), toxin-induced liver disease (such as that caused by alcohol), septic shock, cachexia and anorexia.

Any therapeutic agent known for treating a neoplastic or condition associated with increased apoptosis, cellular death, cellular damage, or combinations thereof, can be used in the disclosed methods. Thus, agents capable of causing cellular death can cause the dying process to begin, for example, by damaging the cell. Moreover, any agent that is capable of causing cellular death and/or damage at a selected site within a subject or combinations thereof can be used. Such agents can be administered to the subject.

Administration means a method of administering to a subject. Such methods are well known to those skilled in the art and include, but are not limited to, administration topically, parenterally, orally, intravenously, intravascularly, intramuscularly, subcutaneously or by aerosol. Administration may be effected continuously or intermittently. A therapeutic agent can also be a dose or radiation administered by methods known in the art.

The administration of a particular therapeutic regimen including an agent or stress capable of causing cellular death, beginning the process of cellular death, or capable of causing cellular damage to a subject can be selected by evaluating the particular aspects of the medical history, signs, symptoms, and objective laboratory tests that are known to be useful in evaluating the status of a subject with cancer, or another apoptosis inducing condition. These signs, symptoms, and objective laboratory tests can vary, depending upon the particular cancer or condition being treated or prevented, as will be known to any clinician who treats such patients or a researcher conducting experimentation in this field. For example, if, based on a comparison with an appropriate control group and/or knowledge of the normal progression of the disease in the general population or the particular individual: 1) a subject's physical condition is shown to be improved, 2) the progression of the disease is shown to be stabilized, slowed, or reversed, or 3) the need for other medications for treating the disease or condition is lessened or obviated, then a particular treatment regimen will be considered efficacious. Such effects could be determined in a single subject in a population (e.g., using epidemiological studies).

A therapeutic regimen can include agent and/or other stressors capable of causing cellular death or cellular damage or combinations thereof. Such agents or stressors may be administered to a subject in an "effective amount," "effective dosage" or "therapeutic amount." The term "effective amount" can be defined as any amount necessary to produce a desired physiologic response. Effective amounts and schedules for administering the therapeutic agents, known as the "therapeutic regimen" used in the disclosed methods can be determined empirically, and making such determinations is within the skill in the art. The effective dosage ranges for the administration of the agents used in the disclosed methods are those large enough to produce the desired effect in which the symptoms of the disorder are affected. The dosage should not be so large as to cause adverse side effects, such as unwanted cross-reactions, anaphylactic reactions, and the like.

Generally, the therapeutic amount or dosage will vary with the age, condition, sex and extent and type of the disease in the subject, route of administration, or whether other drugs are included in the regimen, and can be determined by one of skill in the art. The dosage can be adjusted by the individual physician or veterinarian in the event of any counterindications. A treatment regimen can comprise varying dosages of one or more agents or stressors (i.e. radiation) which, can be administered in one or more dose administrations daily, for one or several days. The effective amount of the agents used in the disclosed methods can vary depending on the method used and on the cancer or condition being treated, the particular chemotherapeutic or other therapeutic agent, and, or carrier used, and mode of administration, and the like. Thus, it is not possible to specify an exact amount for every therapeutic agent. An appropriate amount can be determined, however, by one of ordinary skill in the art.

Thus, for example, therapeutic amounts, effective amounts, or effective dosages of a chemotherapeutic agent used in a therapeutic regimen can be administered by at reasonable intervals and remain effective. For example, an effective dose of such an agent can be administered S.I.D., B.I.D., Q.I.D., or once or more an hour for a day, several days, a week or more. Thus, for example, the agents can be administered once every 1, 2, 4, 8, 12, or 24 hours, or combinations or intervals thereof, for a duration of 1 day, 2 days, 3 days, 4 days, 5 days, 6 days, or for 1 week, 1 month or more or any interval or combination thereof. Furthermore, the agents can be administered once a week, once a month, or any interval or combination thereof. By interval is meant any increment of time within the provided values. Optionally, an agent can be administered once. Such time courses can be determined by one of skill in the art using, for example, the parameters described above for determining an effective dose. Moreover, established protocols or therapeutic regimens for treating a given cancer or condition can be used, or modifications or such regimens can be used.

Figure 26:
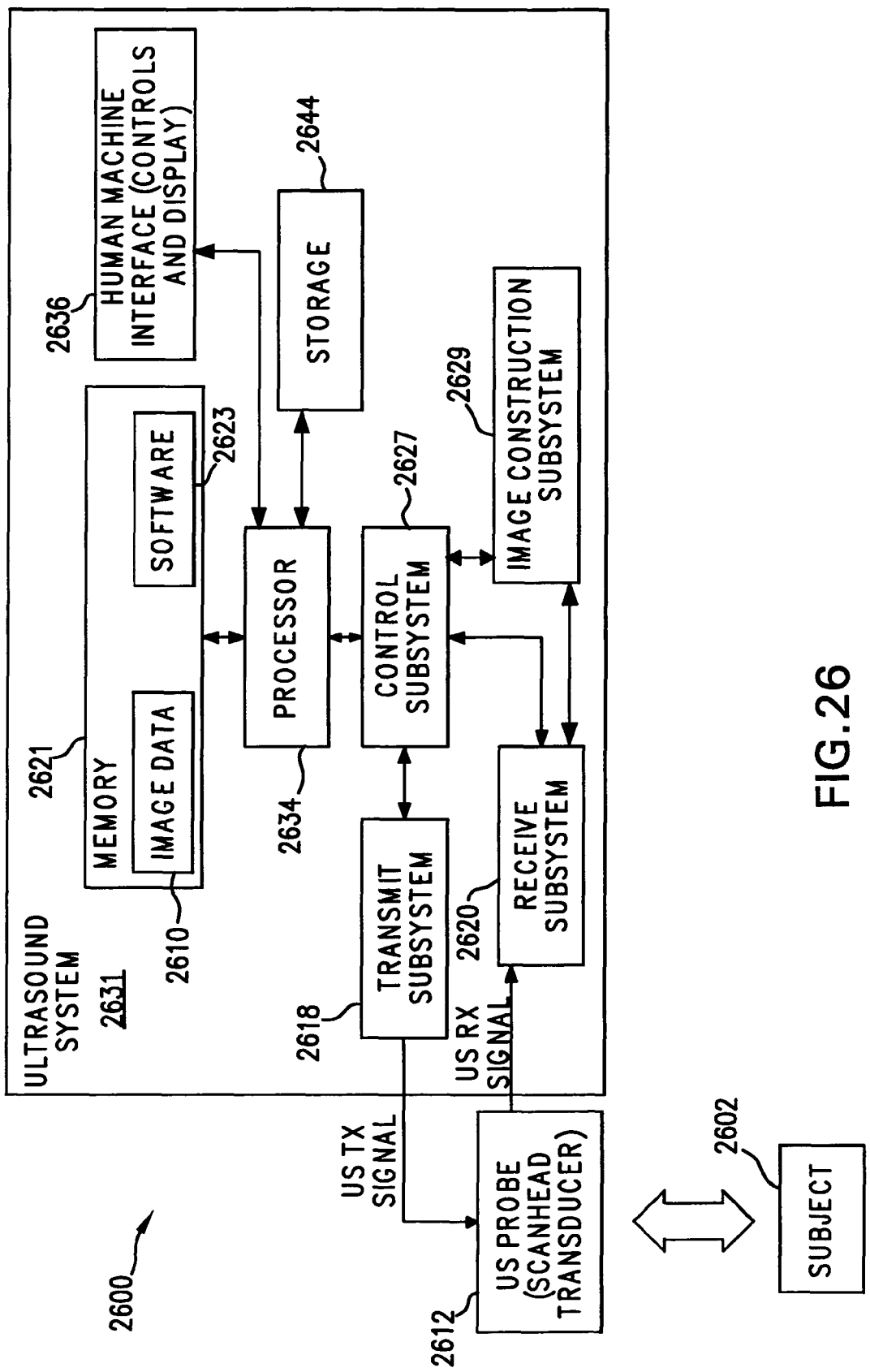
FIG. 26 is a block diagram illustrating an exemplary ultrasound imaging system.

FIG. 26 is a block diagram illustrating an exemplary imaging system 2600 for monitoring cellular death using low frequency ultrasound. The imaging system 2600 can operate on a subject 2602. An ultrasound probe 2612 can be placed in proximity to the subject 2602 to obtain ultrasound image information. The ultrasound probe 2612 can comprise a mechanically moved transducer, or an array that can be used for collection of ultrasound data 2610. For example, the transducer can both transmit ultrasound waves to the subject 2602 and receive ultrasound waves or backscatter from the subject 2602. An ultrasound system 2631 can cause the transducer 2612 to emit ultrasound by sending a transmitter control signal, USTX signal.

The transducer within the probe 2612 can be an array, single element transducer or some other suitable transducer. The transducer can transmit ultrasound at a low frequency, such as frequencies less than or equal to 20 megahertz (MHz). For example, the transducer can transmit ultrasound at or below about 20 MHz, 15 MHz, 10 MHz, 5 MHz, or some other suitable frequency. Further, transducer operating frequencies significantly lower than those mentioned are also contemplated.

The ultrasound system 2631 can include a control subsystem 2627, an image construction subsystem 2629, a transmit subsystem 2618, a receive subsystem 2620, and a user input device in the form of a human machine interface 2636. A processor 2634 can be coupled to the control subsystem 2627 and the display 2616 can be coupled to the processor 2634.

A memory 2621 can be coupled to the processor 2634. The memory 2621 can be any type of computer memory, and can be referred to as random access memory "RAM," in which the software 2623 of the invention executes. Software 2623 controls the acquisition, processing and display of the ultrasound data allowing the ultrasound system 2631 to display an image. The software and/or hardware, and/or a combination thereof, can also allow for the processing and comparison of received backscatter data and for envelope characteristic comparison, as described in the disclosed methods.

The method and system for monitoring cellular death using low frequency ultrasound can be implemented using a combination of hardware and software. The hardware implementation of the system can include any or a combination of the following technologies, which are all well known in the art: discrete electronic components, a discrete logic circuit(s) having logic gates for implementing logic functions upon data signals, an application specific integrated circuit having appropriate logic gates, a programmable gate array(s) (PGA), a field programmable gate array (FPGA), etc.

The software for the system 2600 can comprise an ordered listing of executable instructions for implementing logical functions, and can be embodied in any computer-readable medium for use by or in connection with an instruction execution system, apparatus, or device, such as a computer-based system, processor-containing system, or other system that can fetch the instructions from the instruction execution system, apparatus, or device and execute the instructions.

In the context of this document, a "computer-readable medium" can be any means that can contain, store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium. More specific examples (a non-exhaustive list) of the computer-readable medium can include the following: an electrical connection (electronic) having one or more wires, a portable computer diskette (magnetic), a random access memory (RAM), a read-only memory (ROM), an erasable programmable read-only memory (EPROM or Flash memory) (magnetic), an optical fiber (optical), and a portable compact disc read-only memory (CDROM) (optical). Note that the computer-readable medium can even be paper or another suitable medium upon which the program can be printed, as the program can be electronically captured, via for instance optical scanning of the paper or other medium, then compiled, interpreted or otherwise processed in a suitable manner if necessary, and then stored in a computer memory.

The ultrasound system 2631 can include software 2623 stored in the memory 2621. This software can include system software, as well as, software to process and compare ultrasound backscatter and to formulate images, as described herein, to perform the described methods. The software 2623 can also include envelope statistic determination and/or detection and/or comparison software.

Memory 2621 can also include the ultrasound data 2610 obtained by the ultrasound system 2631. A computer readable storage medium 2638 can be coupled to the processor 2634 for providing instructions to the processor 2634 to instruct and/or configure the processor 2634 to perform algorithms related to the operation of ultrasound system 2631. The computer readable medium can include hardware and/or software such as, by the way of example only, magnetic disk, magnetic tape, optically readable medium such as CD ROMs, and semiconductor memory such as PCMCIA cards. In each case, the medium can take the form of a portable item such as a small disk, floppy disk, cassette, or can take the form of a relatively large or immobile item such as a hard disk drive, solid state memory card, or RAM provided in the support system. It should be noted that the above listed example mediums can be used either alone or in combination.

The ultrasound system 2631 can include a control subsystem 2627 to direct operation of various components of the ultrasound system 2631. The control subsystem 2627 and related components can be provided as software for instructing a general purpose processor or as specialized electronics in a hardware implementation. The ultrasound system 2631 can include an image construction subsystem 2629 for converting the electrical signals generated by the received ultrasound echoes (or backscatter) to data that can be manipulated by the processor 2634 and that can be rendered into an image or graphical depiction on the display 2616. The control subsystem 2627 can be connected to a transmit subsystem 2628 to provide ultrasound transmit signal, USTX signal, to the ultrasound probe 2612. The ultrasound probe 2612 in turn can provide an ultrasound receive signal to a receive subsystem 2620. The receive subsystem 2620 can also provide signals representative of the received signals to the image construction subsystem 2629. The receive subsystem 2620 can be also connected to the control subsystem 2627. The image construction subsystem 2629 can be directed by the control subsystem 2627 to operate on the received data to render an image for display using the image data 2610.

The receive subsystem 2620 can be connected to the control subsystem 2627 and an image construction subsystem 2629. The image construction subsystem 2629 can be directed by the control subsystem 2627. The ultrasound system 2631 can transmit and receive ultrasound data with the ultrasound probe 2612, can provide an interface to a user to control the operational parameters of the imaging system 2600, and can process data appropriate to formulate still and moving images that represent anatomy and/or physiology, and or regions of cellular death and/or regions of interest within the subject that have or have not been exposed to a stress capable of causing cellular death of the subject 2602. Images can be presented to the user through the display 2616.

The human machine interface 2636 of the ultrasound system 2631 can take input from the user and translates such input to control the operation of the ultrasound probe 2612. The human machine interface 2636 can also present processed images and data to the user through a display. Software 2623 in cooperation with the image construction subsystem 2629 can operate on the electrical signals developed by the receive subsystem 2620 to develop an ultrasound image and/or representations and/or comparisons of ultrasound backscatter data received from areas of interest of the subject that have or have not been exposed to a stress capable of causing cellular death.

Figure 27:
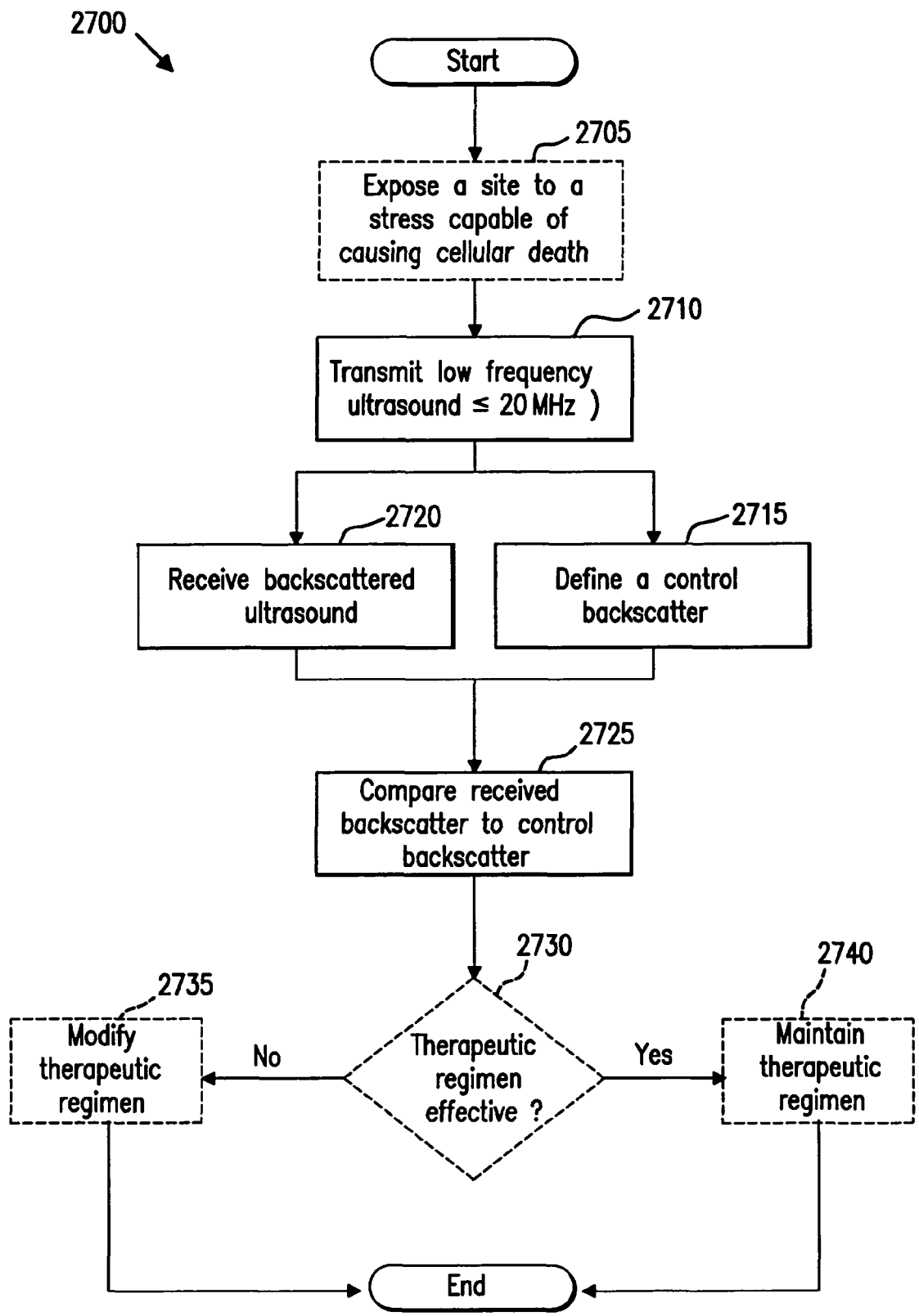
FIG. 27 is a flow block diagram illustrating an exemplary method of monitoring a therapeutic regimen using low frequency ultrasound.

Turning now to FIG. 27, this figure is a flow chart 2700 that controls the operation of the ultrasound system 2631 in detail with reference to FIG. 26. Any process descriptions or blocks in the flowcharts can be understood as representing modules, segments, or portions of code, which can include one or more executable instructions for implementing specific logical functions or blocks in the process. Alternative implementations are included within the scope of the invention in which functions can be executed out of order from that shown or discussed, including substantially concurrently or in reverse order, depending on the functionality involved, as can be understood by those reasonably skilled in the art.

In block 2705, a site can be exposed to a stress capable of causing death. More specifically, this exposure can involve causing an area on, or within, the subject 2602 (see FIG. 26) to be exposed to a therapeutic agent capable of causing cellular death, such as those described herein. Though not shown in FIG. 26, this exposure can occur by administration of an agent, or stressor, capable of causing cellular death to the subject 2602. Because the block 2705 is shown in dashed lines, it indicates that this optional block can occur at some point before the remaining blocks in the flowchart 2700. In addition, this block can also be completed by someone or something external to the ultrasound system 2631 (see FIG. 26), such as a physician or other medical professional.

Low frequency ultrasound can be transmitted at block 2710. Low frequency ultrasound refers to ultrasound with a frequency of less than or equal to 20 MHz. This ultrasound can be transmitted into the subject 2602 at the exposed site described with reference to block 2705. To transmit this low frequency ultrasound, the transducer 2612 can be used in response to receiving the ultrasound transmission signal, US TX signal, from the software 2631 as previously described with reference to FIG. 26.

In the flow chart 2700, block 2715 and block 2720 follow block 2710. However, an alternative embodiment can exist where only block 2720 follows block 2710 because block 2715 can be completed at some earlier point. For example, block 2715 can occur during an initialization period when the transducer 2612 establishes some initial settings. In block 2715, a control measurement for backscatter can be defined based on several characteristics, such as distance between the transducer 2612 and the subject 2602, frequency of the ultrasound, and other suitable factors. This control backscatter measurement can be determined as described herein.

In block 2720, at least a portion of the backscattered ultrasound from the exposed site can be received by the transducer 2612. As described with reference to FIG. 26, this received backscattered ultrasound can be associated with the ultrasound receive signal, US RX signal, that can be received by the software 2623.

The received backscatter measurement can be compared to the control backscatter measurement at block 2725. To interpret the comparison between the control backscatter and the received backscatter any one of numerous conventions can be used. For example, one interpretation convention can be that either an increase or a decrease in the received backscattered ultrasound when compared with the control backscatter measure indicates cellular death and or/damage at the exposed site within the subject 2602. For this convention, an increase in the received backscattered ultrasound can correspond to an increase in an intensity measurement of the received backscattered ultrasound when compared to an intensity measurement of the control backscatter measurement. An alternative interpretation convention can be that a spectral slope of the received backscattered ultrasound can be compared to a spectral slope from the control backscatter measurement. For this convention, a modulation in the received backscattered ultrasound spectral slope when compared with the spectral slope of the control backscatter measurement can indicate cellular death and/or damage. Alternatively, either an increase in the spectral slope of the received backscatter or a decrease in the spectral slope of the received backscatter can indicate cellular death and/or damage.

The remaining blocks in flow chart 2700, which are optional, assess whether a therapeutic regimen should be maintained or modified based on the comparison completed in block 2725. In block 2730, the effectiveness of the therapeutic regimen can be determined based on whether cellular death and/or damage has been indicated. If the therapeutic regimen is not effective, it can be modified at block 2735. If it is determined at block 2730 that the therapeutic regimen is effective, then this regimen can be maintained at block 2740. The flowchart 2700 ends after either block 2735 or block 2740 is completed.

Though not shown, an alternative embodiment to the flowchart 2700 can exist where first and second images are formed of the exposed site. More specifically, the transmission of low frequency ultrasound at block 2710 results in forming a first image of the exposed sight. At some subsequent time, a second image of the exposed site can be taken. A signal amplitude can be measured for a first region of interest and a second region of interest respectively associated with the first and second images. The comparison at block 2725 can compare the signal amplitude of the first and second images to determine if cellular death and/or damage occurred.

Figure 28:
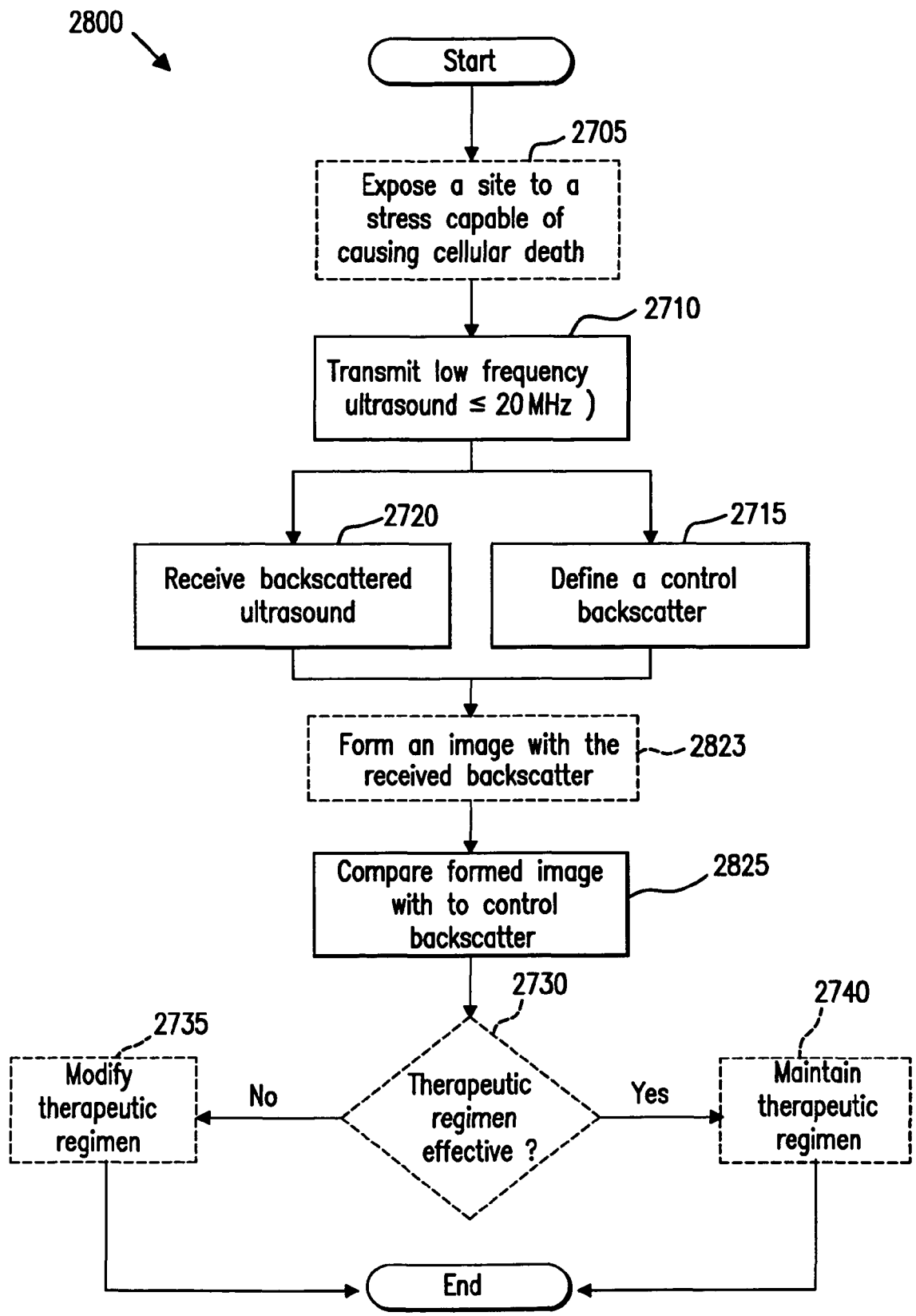
FIG. 28 is a flow block diagram illustrating an exemplary method of monitoring a therapeutic regimen using low frequency ultrasound.

FIG. 28 is a flowchart 2800 illustrating an alternative embodiment for the flowchart 2700 described with reference to FIG. 27. Because similar blocks are shown with similar numbers that have been described, only differing blocks are described.

Block 2823 can follow block 2715 and block 2720, in which, an image can be formed with the received backscatter. More specifically, this block can involve processing the received backscatter measurements to form an image that can be displayed on the human machine interface 2636 described with reference to FIG. 26. For the sake of brevity, the extensive details involved in generating an image from backscatter ultrasound data is omitted because they would be understood by one skilled in the art of ultrasound imaging.

In block 2825, the formed image can be compared to the ultrasound to the control backscatter. For this embodiment, the control backscatter can refer to a control image generated by using control backscatter data. The control image can be generated in a manner similar to the manner that the image is formed using the received backscatter data. As described with reference to block 2725 in FIG. 27, any one of several interpretation conventions can be used in block 2825. For example, an increase in the ultrasound image formed from the received data when compared to the control image can indicate cellular death and/or damage at the exposed site within the subject 2602. In addition, an increase in the ultrasound backscatter of the formed image can be an increase in the intensity of the backscatter, while a decrease in ultrasound backscatter can be decrease in intensity of the backscatter of the formed image. The remaining blocks in the flowchart 2800 operate identically to previously described blocks and are not described again here.

Figure 29:
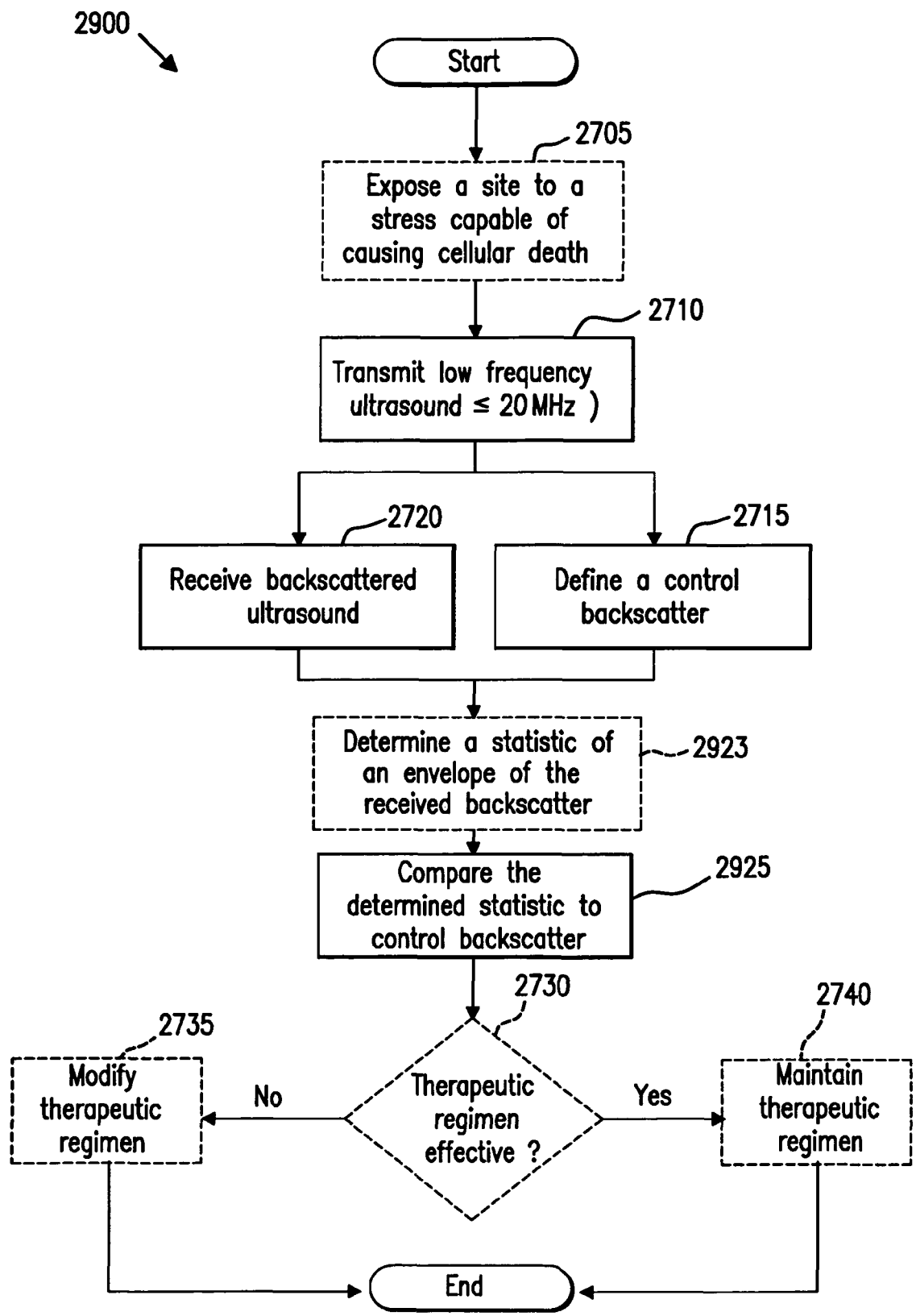
FIG. 29 is a flow block diagram illustrating an exemplary method of monitoring a therapeutic regimen using low frequency ultrasound.

Turning now to FIG. 29, this figure is a flowchart 2900 illustrating a second alternative exemplary embodiment for the flowchart 2700 described with reference to FIG. 27. Because similar blocks are shown with similar numbers that have been described, only differing blocks will be described.

At block 2923, an envelope statistic can be determined for the received backscatter as described herein. Because the received backscatter can be formed from numerous data points, a statistic envelope can be determined. For the sake of brevity, the extensive details involved in determining a statistic envelope is omitted because they would be understood by one skilled in the art of both ultrasound imaging and mathematics. The determined statistic can be compared to the control backscatter at block 2925. Either an increase or decrease of the determined statistic when compared with the control can indicate cellular death. The remaining blocks in the flowchart 2900 can operate identically to previously described blocks and are not described again here.

The present invention can be applied to several different ultrasound imaging methods. These methods include the use of external transducers that can be used to image superficial tissues such as the skin and eye or deep tissues including tissues or cells that are deeper than the effective penetration depth of ultrasound with a frequency above 20 MHz, invasive interstitial needle-based transducers that can be inserted directly into a target tissue deep within the body such as a tumor or normal tissue, intraluminal catheter-based transducers that are designed to image from within arteries for example and endoscopic or intracavitary ultrasound systems that can be used to image tissues including the esophagus and colon for example.

EXPERIMENTAL

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

A backscatter signal can be composed of contributions from many individual scatterers. Each scatterer contributes an amplitude and a phase to the received signal. This can be modeled by equation 1 (Raju and Srinivasan, 2002):

$$re^{j\Psi} = \sum_{i=1}^{n} r_i e^{j\theta_i}. \quad (1)$$

The amplitude and the phase ($r_i$ and $\theta_i$) contribution from each scatterer can be determined by its position, size and acoustic properties. As there can be a statistical distribution of these properties, the amplitude and phase (r and $\Psi$) of the received signal can also have a probability distribution. Numerous probability density functions (PDFs) have been proposed to describe the statistics of ultrasonic backscatter (Dutt and Greenleaf, 1994; Narayanan et al., 1994; Shankar et al., 1996; Raju and Srinivasan, 2002). Two of these distributions, the Rayleigh distribution (Strutt, 1880) and the generalized gamma (GG) distribution (Stacy, 1962) can be used in the described methods.

The Rayleigh PDF, often used as a simplified description of the statistics, is based on three assumptions. First, the scatterers are much smaller than the wavelength. Second, the resolution cell of the ultrasound system, in this case of lateral dimension 250 µm and axial 140 µm, contains a large number of scatterers. Finally, the scatterers are located randomly in the medium. Where the cells in a pellet are compacted side-by-side, it can be considered that the major acoustic interface is the cytoplasm-nucleus boundary. Experimental evidence suggests that, the nucleus is the primary scatterer (Czarnota, 2002; Beaulieu et al., 2002). In the AML cells used, the nucleus is approximately 9 µm in diameter, smaller than the wavelength range of 50-150 µm. Furthermore, if one assumes there is one scatterer per cell, then there are approximately 4600 scatterers per resolution volume. However, there can be some inherent degree of organization of the cells within a pellet, making it not a completely random medium. The Rayleigh PDF is given in equation 2:

$$p(r) = \frac{r}{\sigma^2} e^{\frac{-r^2}{2\sigma^2}} \quad (2)$$

$$r \geq 0; \sigma > 0$$

where the probability, p, of a Rayleigh-distributed signal having an amplitude r is a function of the scale parameter, $\sigma$, which represents a measure of the mean signal amplitude. The GG PDF was first proposed by Stacy (1962). Its application to modeling ultrasound signals was proposed independently by Raju and Srinivasan (2002) and Shankar (2001b). The GG PDF is given in equation 3.

$$p(r) = \frac{cr^{cv-1}}{a^{cv}\Gamma(v)} e^{-\left(\frac{r}{a}\right)^c} \quad (3)$$

$$r \geq 0; a \geq 0; v \geq 0; c \geq 0$$

where $\Gamma(v)$ is the incomplete gamma function, a is the scale parameter, which is related to the mean of the PDF, while c and v are two shape parameters, representing the positions of the left and right tail of the PDF, respectively. The GG PDF is equivalent to a number of other PDFs as special cases, including the Rayleigh when c=2 and v=1. The GG PDF is similar to the generalized Nakagami PDF proposed by Shankar (2001b) to model ultra-sound statistics. In the context of the generalized Nakagami PDF, Shankar (2001b) has proposed that the scale parameter (a) is a measure of average backscattered power, and can be related to the average scatterer cross-section (Shankar, 2001b). As described by Hunt et al. (2002), the average backscattered power is dependent on both the geometrical cross-section and scatterer organization, and therefore a parameter reflects both. Based on the interpretation proposed by Shankar (2001b), the shape parameters of the GG PDF (c and v) relate to the scatterer number density. The ratio of the two parameters, c/v, can be used as an estimate of effective scatterer number density. Recent experimental evidence indicates that in the in vitro model of cells in suspension at low volumetric concentrations, this interpretation of the parameters the GG PDF does apply to a biological model. Each of the above envelop signal statistics/parameters and/or ratios thereof can be used in the disclosed methods.

Example 2

The response of the HEP-2 cell line (a Human Caucasian larynx carcinoma cell line) to the chemotherapeutic drug camptothesin, shown to induce apoptosis in this cell-line was determined.

HEP-2 cell death induction: For the induction of apoptosis, cells were incubated at 37° C. and 5.0% $CO_2$ in 30 μg/mL of camptothecin for various timepoints up to 48 hrs. Pipetting an appropriate amount of the reagent and dissolving it in MEM with 0.1% gentamycin prepared the camptothecin solution. The camptothecin solution was prepared fresh for each experiment. After the treatment, cells were washed with phosphate buffered saline (PBS) and detached using trypsin. These were then pelleted in flatbottom cryotubes at 1500 g on a desktop swinging bucket centrifuge with a diameter and height of approximately 1 cm. Pellets were imaged with a 20 or 40 MHz transducer, and RF data were collected.

FIG. 1 shows exposure of HEP2 cells to the chemotherapeutic camptothesin. Pellets of unexposed cells imaged at 20 MHz (A) and 40 MHz (B) and camptothesin exposed cells (24 hour exposure) imaged at 20 MHz (C) and 40 MHz (D). Spectroscopic data (E) collected with the 20 MHz (10-30 MHz band) and 40 MHz (20-56 MHz band) transducers, before treatment (0 h) and at a series of timepoints (6 h, 17 h, 24 h, 48 h) after treatment. Whereas an increase in backscatter is observed at 20 MHz (upwardly pointing arrow), at 40 MHz a gradual decrease (downwardly pointing arrow) is observed. A reduction in spectral slope is also observed.

Example 3

The response of NHL cells (Non-Hodgkins Lymphoma, human B cell lymphoma established from the pleural effusion of a 46-year-old woman with nodular histiocytic lymphoma) to CHOP chemotherapy are demonstrated, both in-vitro (Daunorubicin 0.012 mM, Cyclophosphamide 0.35 mM, Vincristine 0.2 nM, Prednisone 0.037 mM) and in-vivo in an animal model (table 4.1).

NHL cell death induction: Non-Hodgkin's Lymphoma cells (CRL2261, American Tissue Culture Collection) were cultured, then a concentration of $10^6$ cells in 50 μl of media was injected intra-dermally into the left hind leg of severe combined immunodeficiency disease (SCID) mice, or were grown to form pellets. Primary tumors were allowed to develop for approximately 4 weeks, until they reached a diameter of 8-10 mm. The mice/cells were treated with the CHOP chemotherapy regimen, as is used clinically to treat aggressive NHL. In this regimen four drugs (Cyclophosphamide, Hydroxydoxorubicin, Vincristine (Oncovin) and Prednisone) were injected with a 15 minute separation between drugs, in doses outlined in Table 4.1. Prednisone was injected daily during the treatment, while the other drugs were injected at the beginning of the treatment. As a control, other animals received injections of saline following the same injection procedure as the treated animals.

Table 4.1: Doses administered to mice in the CHOP regimen. Each drug was diluted in saline to a total volume of 300 μl for a 25 g mouse.

TABLE 4.1

Doses administered to mice in the CHOP regimen. Each drug was diluted in saline to a total volume of 300 μl for a 25 g mouse.

| Drug | Dose [$mg/m^2$] |
|---|---|
| Cyclophosphamide | 750 |
| Hydroxydoxorubicin | 50 |
| Vincristine | 1.4 |
| Prednisone | 100(Daily) |

Prior to the imaging procedure the hair on the tumor was removed with a depilatory (Neet™, Reckitt-Benckiser, UK). The animals were then anaesthetized for the imaging procedure. For most procedures a mixture of drugs (100 mg/kg Ketamine, 5 mg/kg Xylasine and 1 mg/kg Acepremazine diluted with saline to 0.1 ml) was injected subcutaneously as this sedated the mouse for approximately 1.5 hours, sufficient time for the entire imaging procedure. However when imaging was performed at multiple times for the same animal an inhaled anaesthetic (halothane) was administered to reduce the stress on the animal of multiple injections at short time intervals. The mouse was placed in a restraint which held the tumor submerged in a heated water bath but elevated the head out of the water The tumors of 12 animals were each imaged before the treatment and at time points up to 96 hours after the beginning of the treatment. The tumors of four additional mice were imaged at multiple timepoints during the treatment, to monitor the changes as they occurred within one animal. B-scan images and RF data were acquired from the tumor using the 20 MHz f#2.35 transducer. Approximately 200 RF lines separated by at least one beamwidth were acquired from five imaging planes within the tumor. Care was taken to ensure the imaging procedure was performed in the same region of the tumor at all time points during the treatment. Animals were sacrificed at various time points and tumor tissue was extracted and fixed for H&E and TUNEL staining.

FIG. 2 shows pellets of NHL cells, imaged using a 20 MHz ultrasound transducer, before treatment (A) and 16 hours after treatment using CHOP chemotherapy (B). The transducer focus in located about 1 mm below the pellet surface. Spectroscopic data collected with the 20 MHz (10-30 MHz band) and 40 MHz (20-56 MHz band) transducers, before treatment and 12 hours after CHOP chemotherapy. The overlap of the data between 20 MHz and 30 MHz provides confidence in the measurement technique. An increase is backscatter is observed, with a concomitant decrease in the spectral slopes for both the 20 and 40 MHz transducers.

FIG. 3 shows ultrasonic images (20 MHz transducer) of the NHL implanted tumor of the same animal before treatment (A) and 12 hours after treatment (B). An increase in backscatter is observed. Spectroscopic data collected with the 20 MHz (10-30 MHz band) and 40 MHz (20-56 MHz band) transducers, before treatment and 12 hours after CHOP chemotherapy.

Example 4

Data were acquired using the VisualSonics VS-40B scanner (VisualSonics Inc., Toronto, Ontario, Canada) modified to acquire raw RF data along with B-scan images. Several transducers also manufactured by VisualSonics were used to acquire data, the characteristics of these are listed in Table 3.1

TABLE 3.1

Characteristics of transducers used in data acquisition.

| Transducer | 074-20-20 | F2-30-03 | 103-40-6 |
|---|---|---|---|
| Centre Frequency | 20 MHz | 30 MHz | 40 MHz |
| Focal Length | 20.00 mm | 12.75 mm | 9.00 mm |
| f# | 2.35 | 2.13 | 3 |
| Lateral Resolution | 247 μm | 149 μm | 157 μm |
| Axial Resolution | 135 μm | 54 μm | 45 μm |
| Depth of Field | 3.12 mm | 1.72 mm | 2.50 mm |
| λ in water | 75 μm | 50 μm | 37.5 μm |
| # of Cells per Resolution Volume | 4660 | 680 | 630 |

Figure 4:
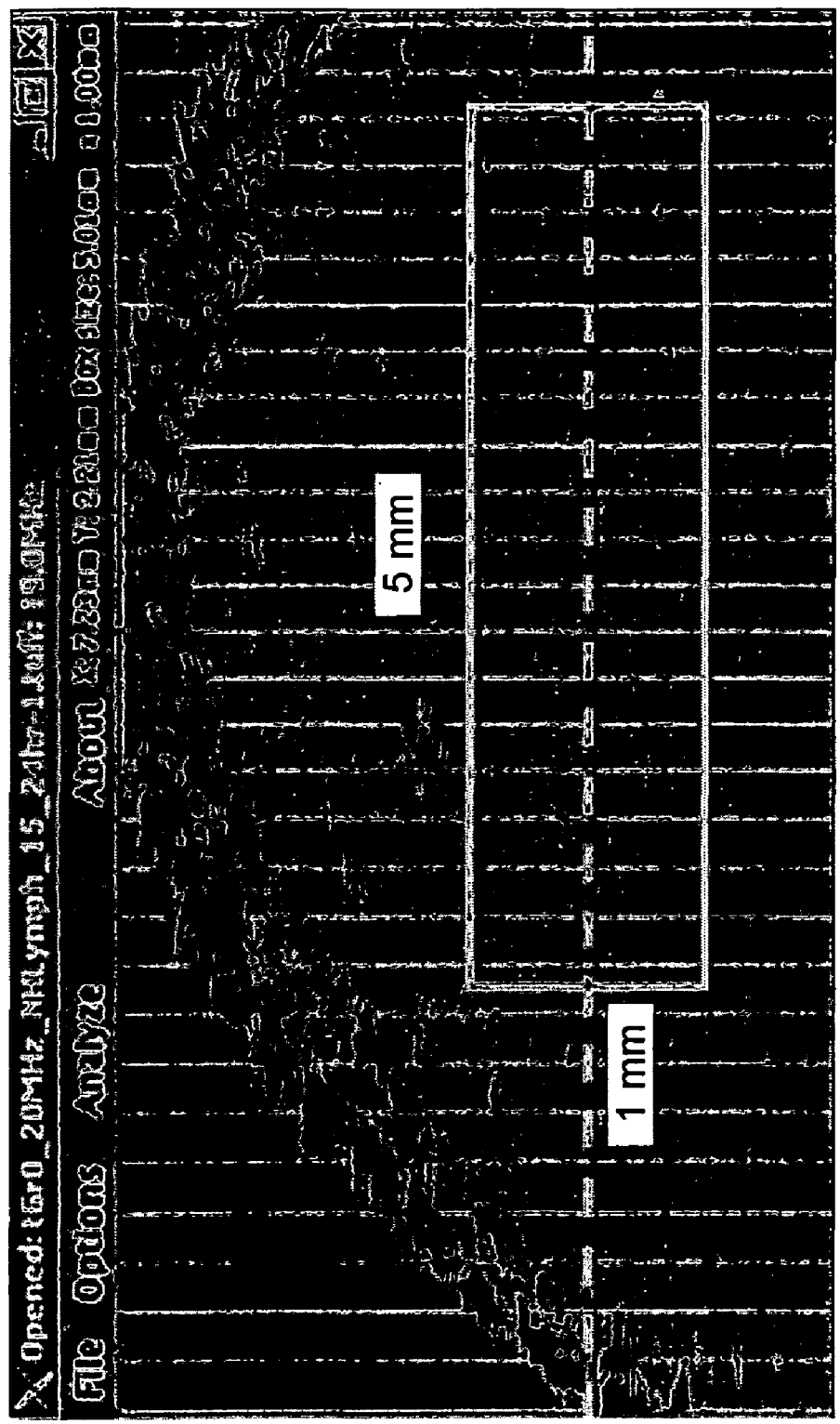
FIG. 4 shows a screen capture of JAVA software used for offline analysis of TUFF files. In this case the file is from a non-Hodgkin's lymphoma tumor implanted in the hind leg of a mouse. The bright band at the upper surface of the tumor is the reflection off the skin of the mouse. The dashed horizontal line shows the focus of the transducer, the vertical lines the location of the acquired RF lines, and the box shows the selection of a homogeneous ROI around the focus for analysis.

A region of interest (ROI) was selected in the B-scan image then RF data were acquired from up to 256 lines separated by at least one beamwidth within the ROI. The RF data were stored in tagged ultrasound file format (TUFF) along with details of the acquisition including the transducer used, the acquisition settings and a B-scan image of the ROI. Using a program written in JAVA (JDK 1.4.1, Sun Microsystems, Inc., Santa Clara, Calif., USA), the TUFF file was reopened and the B-scan ROI displayed along with the focus of the transducer and the location of the RF lines (FIG. 4). Within the file, a homogeneous ROI 1 mm deep centered on the focus was selected. The RF data from this ROI were then extracted and the gain applied during acquisition removed. The extracted data were saved as text files for analysis with Matlab (The MathWorks Inc., Natick, Mass., USA).

FIG. 4 shows a screen capture of the JAVA software used for offline analysis of the TUFF files. In this case the file is from a non-Hodgkin's lymphoma tumor implanted in the hind leg of a mouse. The bright band at the upper surface of the tumor is the reflection off the skin of the mouse. The dashed horizontal line shows the focus of the transducer, the vertical lines the location of the acquired RF lines, and the box shows the selection of a homogeneous ROI around the focus for analysis.

After extraction of the RF data from the TUFF files, the rest of the analysis was done in Matlab (The MathWorks Inc., Natick, Mass., USA) using the Statistics, Optimization, Symbolic and Signal toolboxes. Before the analysis the data were corrected for attenuation. Since the data were selected from a 1 mm deep ROI centered on the focus, which is well within the depth of field of all the transducers used in the experiments (Table 3.1), any drop in signal over the depth of the ROI was due mainly to the effect of attenuation. To correct for this, the attenuation in dB/mm was determined as the decrease in mean signal envelope over the 1 mm depth. Using this attenuation value the data were corrected for attenuation by applying depth dependant amplification. The trends observed were not significantly changed when attenuation correction was not applied. To obtain the fit parameter values of the theoretical PDFs to the acquired data, the maximum likelihood estimation (MLE) technique was implemented in Matlab (The MathWorks Inc., Natick, Mass., USA). This is an iterative process using the Nelder-Mead Simplex method to optimize the fit.

The Kolmogorov-Smirnov (KS) goodness of fit test was used to monitor the ability of the different distributions to provide a fit to the data. It is different from the Chi$^2$ test as it is based on the maximum difference between the theoretical and empirical cumulative density functions as opposed to the standard deviation of the data. The benefit of using the KS test is that it gives a critical value (CV) against which to compare the result obtained.

Figure 5:
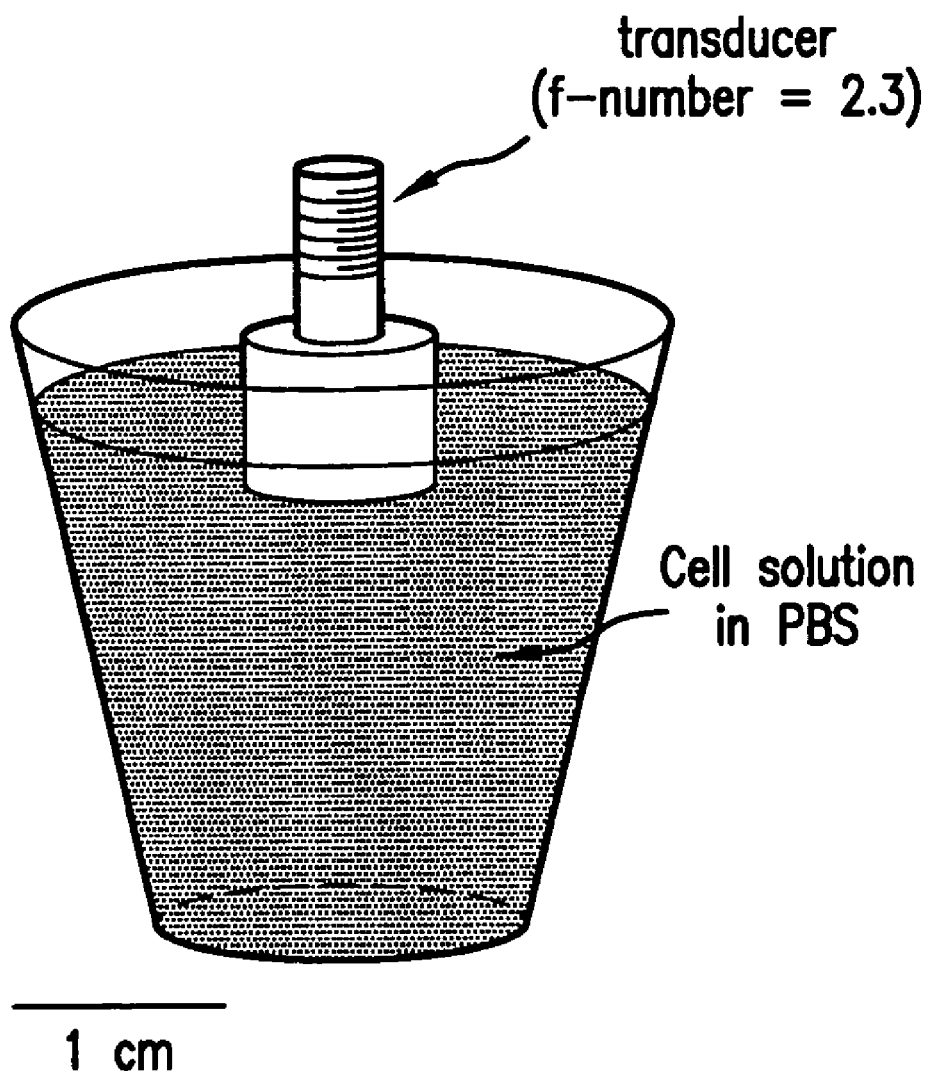
FIG. 5 shows the schematic of setup for cell dilution experiments. A set volume of cells were placed in a plastic container filled with PBS to generate solutions with a known concentration of cells.

Dilutions of two different sized cell lines in suspension were used. Separate cultures of acute myeloid leukemia cells (OCI-AML5) and prostate adenocarcinoma cells (PC-3) were grown. The AML cells were grown at a cell density of $3 \times 10^5$ cells/ml in α minimum essential medium (GIBCO 11900, Rockville, Md., USA) supplemented with 5% fetal bovine serum (Cansera International, Etobicoke, ON, Canada) at 37° C. The PC-3 cells were grown in Kaighn's modification of Ham's F12 medium (GIBCO 21127, Rockville, Md., USA) supplemented with streptomycin (100 mg/L) and penicillin (100 mg/L) and 10% fetal bovine serum (Cansera International, Etobicoke, ON, Canada) at 37° C. As the PC-3 cells are adherent, before the cells were trypsinized. A volume of each type of cells was measured, then diluted with a corresponding volume of phosphate buffered saline (PBS) solution in a sample holder to form suspensions with various volume concentrations of cells. B-scan images and RF data from approximately 200 locations separated by at least one beamwidth were acquired from the samples of cells (FIG. 5).

Following the data acquisition, images of the individual cells were acquired with a light microscope to estimate the cell diameter. A set volume of cells were placed in a plastic container filled with PBS to generate solutions with a known concentration of cells.

Figure 6A:
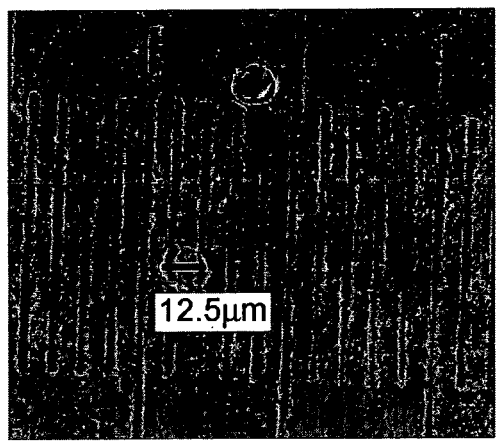
FIG. 6 shows phase contrast light microscopy images of AML cells (A), and PC cells (B). The images are superimposed on a scale bar where every minor division is 10 μm, the AML cells have an average diameter of 12.51 μm while the PC-3 cells have an average diameter of 30 μm.
Figure 6B:
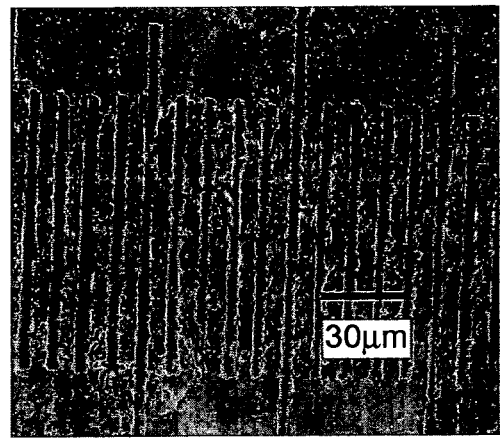
Figure 8B:
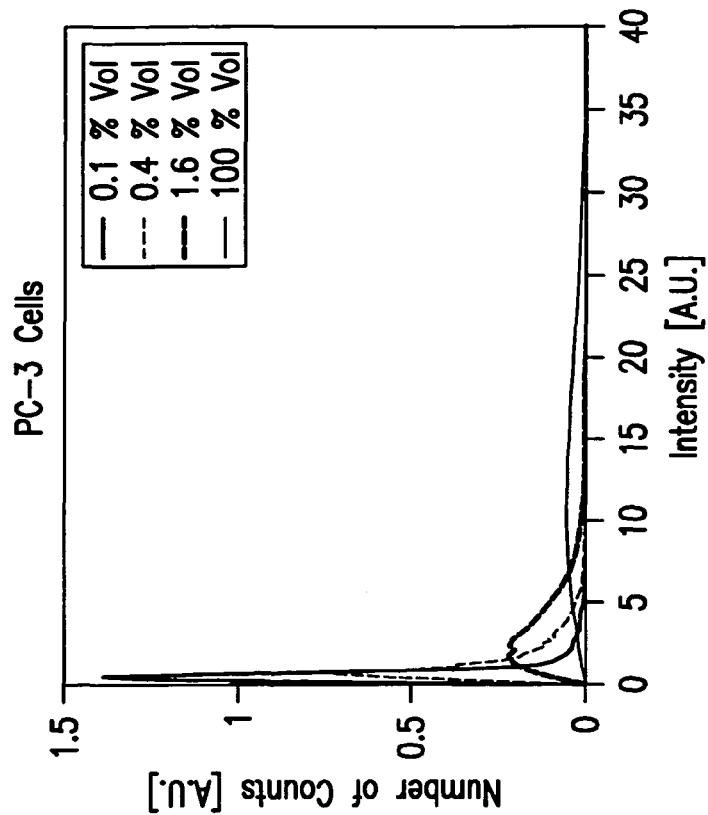
FIG. 8 shows histograms of signal amplitude for AML (A) and PC-3 (B) cells in suspension at various volumetric concentrations and pellets (100% cells). The histograms are normalized to an area of one. The shape of the histogram progresses to higher mean values for all concentrations in solution. While the PC-3 pellet has a higher mean than the PC-3 solutions, the AML pellet has a lower mean than the AML 1.6% solution.
Figure 8A:
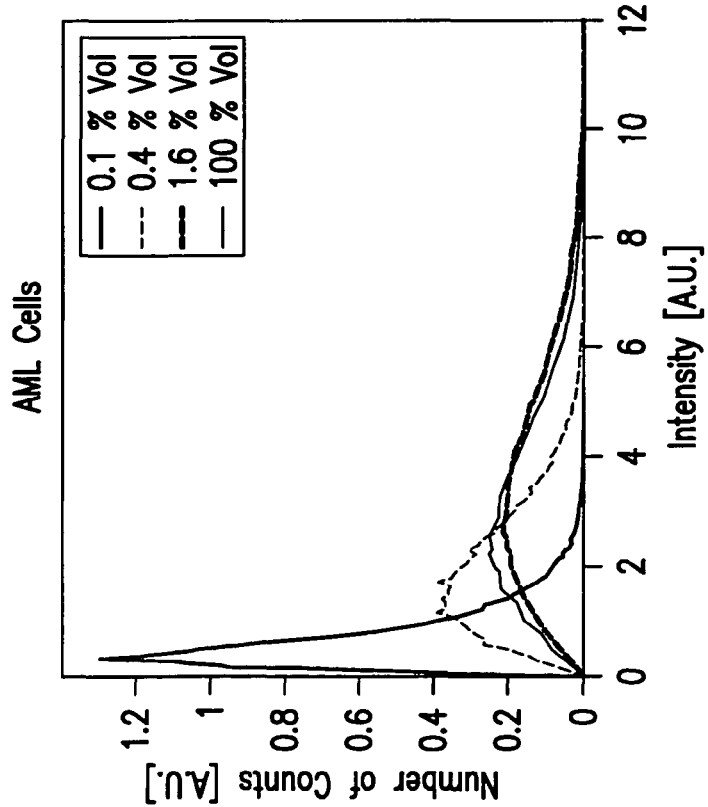

The light microscopy images (FIG. 6) reveal the large difference in diameter of the two cell lines. Because of the larger size of the PC-3 cells, at the same volume concentration of cells, the suspension of AML cells have 14 times more cells per volume than the corresponding suspension of PC-3 cells. This is clearly visible in the B-scan images where at the low volumetric concentrations, such as 0.025%, individual cells are visible in the image (FIG. 7). As the concentration of cells increases the image formed displays a speckle pattern formed from signal contributions from a large number of cells within the resolution volume of the transducer. As the volumetric concentration of cells in the solution is increased up to 1.6% cells by volume the mean of the signal increases. This is also reflected in the shape of the histograms of the signal amplitude for both cell lines (FIG. 8). While the PC-3 pellet has a higher mean signal intensity than the PC-3 1.6% solution, the AML pellet has a lower mean signal intensity than the AML 1.6% solution due to the different scattering interactions for cells in solution and cells in a pellet. The GG PDF fit parameters were determined for the data acquired from the cells in suspension and in pellets. By plotting the GG PDF fit parameters against the calculated number density instead of volumetric concentration certain trends became apparent. The number density was determined based on the concentration used and assuming cell diameters of 12.5 μm and 30 μm for the AML and PC-3 cells respectively. For example, a solution containing 1.6% by volume of 12.5 μm cells, would have $$\frac{0.016}{\frac{4}{3}\pi(12.5 \times 10^{-6})^3} = 2 \times 10^{12} \text{ cells/mm}^3.$$

Figure 9:
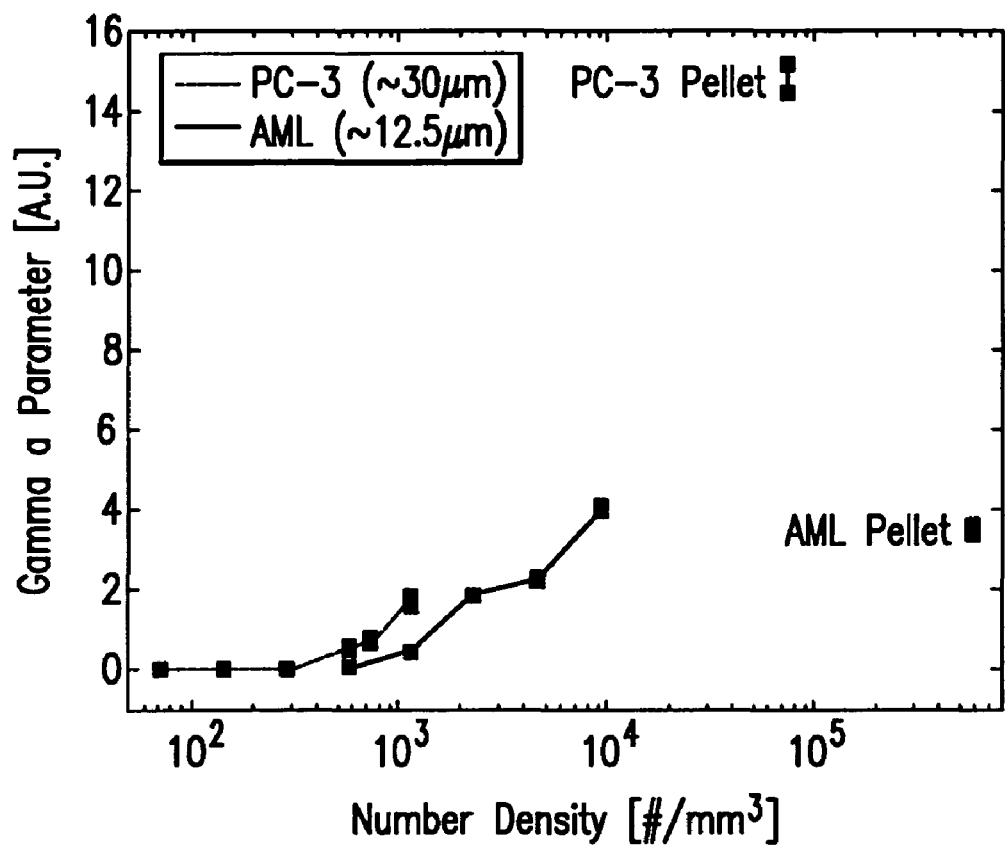
FIG. 9 shows the GG a parameter with 95% confidence intervals for ultrasound data from suspensions of various concentrations of AML and PC-3 cells in PBS. The number density was determined based on the concentration used and assuming uniform cell diameters. The GG a parameter is higher at every number density for the larger PC-3 cells than the smaller AML cells. This agrees with the interpretation of GG a as the effective scatterer cross-section.

The GG a parameter, representing effective scatterer cross-section, increases with the number density of cells in suspension (FIG. 9). As well, at the number densities where the AML and PC-3 overlap, the GG a parameter for the PC-3 cells was larger than the GG a parameter for the AML cells. As the diameter of the PC-3 cells is more than twice that of the AML cells, it is expected that they have a larger effective scatterer cross-section. While the trend does not continue from cells in suspension to cells in pellets, the PC-3 cells do have a higher a parameter than the AML cells.

Figure 10:
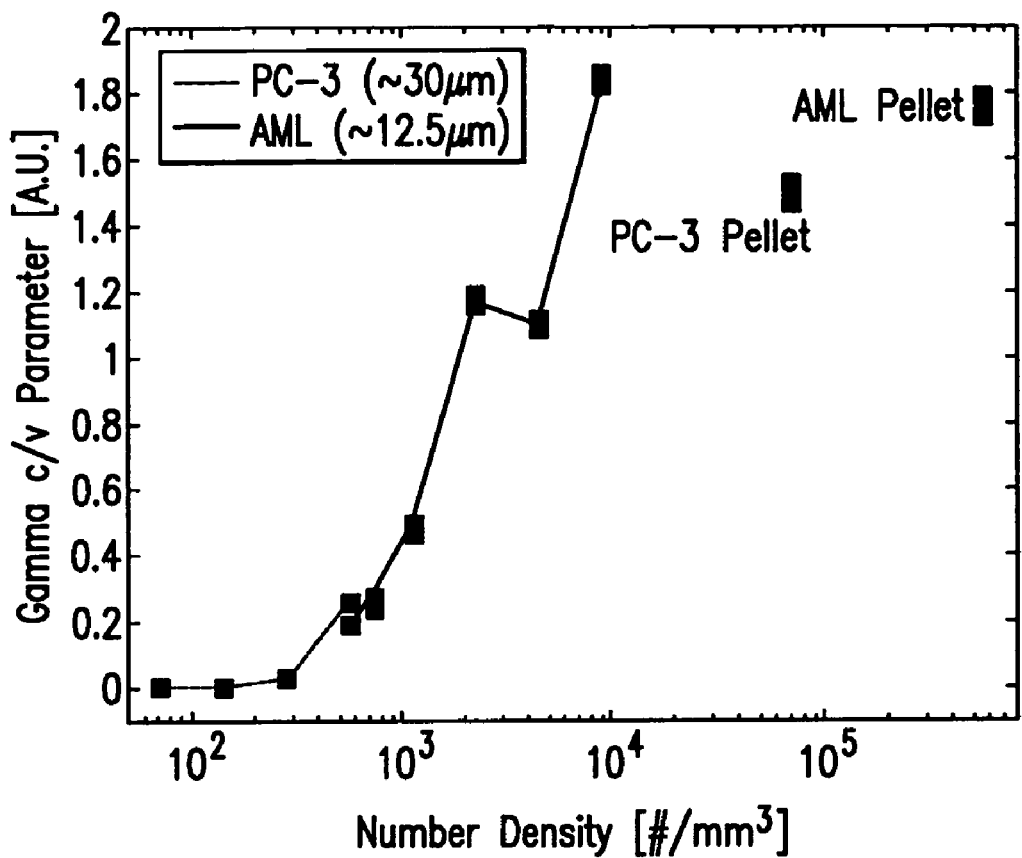
FIG. 10 shows the GG c/v parameter with 95% confidence intervals for ultrasound data from suspensions of various concentrations of AML and PC-3 cancer cells in PBS. The number density was determined based on the concentration used and assuming uniform cell diameters. The GG c/v parameter increases with increasing number density for both cell types. This agrees with the interpretation of the GG c/v as corresponding to effective scatterer number density.

The GG c/v parameter also shows an increasing trend with increasing number density. There is a considerable overlap between the two cell lines in the range where the number densities are similar (FIG. 10). The results indicate that in sparse solutions of cells the c/v parameter can provide an estimate of scatterer number density independent of the size of the scatterers being evaluated. The c/v parameter relates to the effective scatterer number density. Again the trend does not continue from cells in suspension to cells in pellets, however as expected, the AML cells do have a higher c/v parameter than the PC-3 cells.

To demonstrate the use of signal envelope statistics to monitor structural changes in cells during cell death, an in vitro model was used. AML cells were exposed to cisplatinum, a chemotherapy drug, for different amounts of time. Following exposure to cisplatinum backscatter data were collected from pellets of treated cells.

Figure 11:
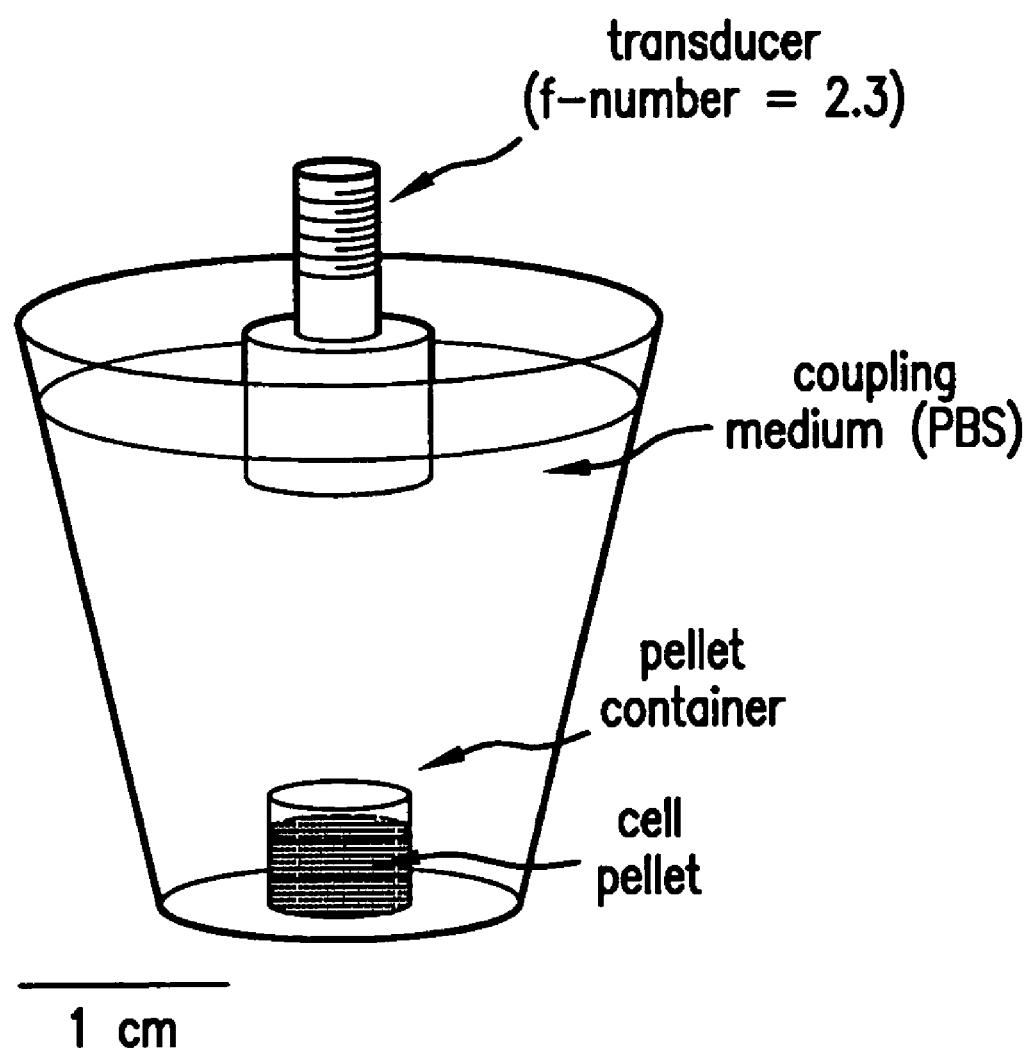
FIG. 11 shows a schematic of a setup for cell pellet experiments. The pellet container was affixed to the bottom of a plastic cup with vacuum grease then the cup was filled with PBS which was used as a coupling medium to the transducer. The transducer was scanned linearly across the pellet generating images of lateral cross-sections through the pellet.

AML cells were cultured at a cell density of $3 \times 10^5$ cells/ml in α minimum essential medium (GIBCO 11900, Rockville, Md., USA) supplemented with 5% fetal bovine serum (Cansera International, Etobicoke, ON, Canada) at 37° C. Cells were treated for 3, 6, 9, 12, 18, 24 and 48 hours with 10 μg/ml of cisplatinum. The cells were then centrifuged in a swinging bucket centrifuge for 10 minutes at 2000 g to form pellets, a compacted aggregate of cells, emulating the cell packing in tissues. The pellets enclosed in the plastic sample container were affixed with vacuum grease to the bottom of a plastic cup. The container was filled with PBS as a coupling medium between the pellet and the transducer (FIG. 11). Several B-scan images were saved, and RF data was acquired from approximately 200 locations separated by at least one beamwidth within the pellet.

Following the data acquisition the pellets were fixed in a 10% formalin solution (Fisher Scientific) for a minimum of two days. The fixed pellet of cells was carefully removed from the pellet holder and placed in a dish of agar gel so that the shape of the pellet was preserved. The pellet was sectioned and placed in a cassette for paraffin embedding so that microtome sections were taken from the same plane as the images. The sections were stained with Haemotoxylin and Eosin (H&E) to examine cell morphology changes.

Figure 13:
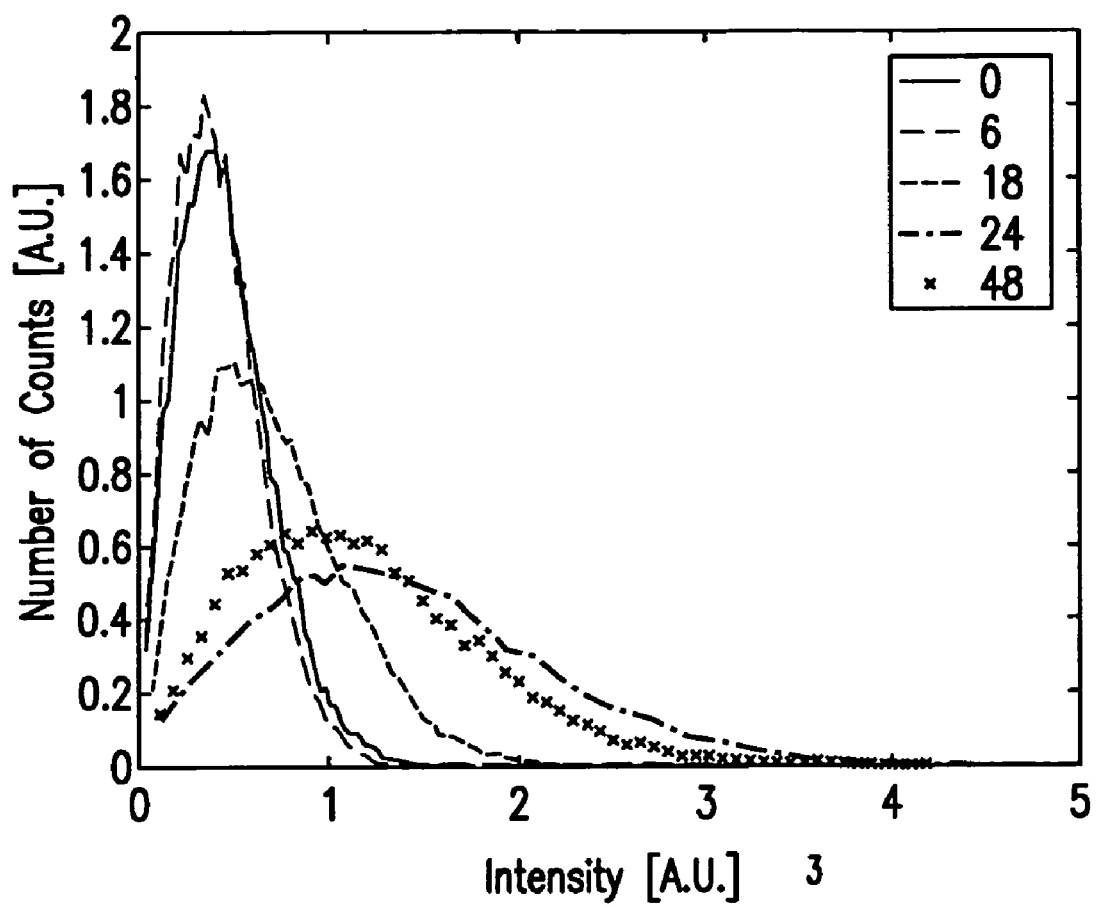
FIG. 13 shows histograms for ultrasound data acquired from pellets of cells treated for 0, 6, 18, 24 and 48 hours with cisplatinum. The large change in scale corresponds to the increase in backscatter intensity. There are also more subtle changes to the shape of the histograms as the cells are treated for longer times, as indicated by changes in the c/v parameter.

As the cells were exposed to cisplatinum, a number of changes occur to cellular and nuclear structure (FIG. 12). These include condensation of the nuclei, as shown in FIG. 12, a sign of cell death. At early time points where there were no visible changes in histology, no changes were apparent in the signal. When cells were treated for longer periods of time there were visible changes in histology, and a marked increase in the backscattered intensity, with a maximum increase of approximately 13 dB between the untreated sample and the sample treated for 24 hours. The marked increase in IB is also apparent in the change in the scale of the histograms of the ultrasound data (FIG. 13). At all exposure times the Rayleigh and GG distribution both provided reasonable fits to the data as determined by the KS goodness of fit parameter. The GG provided a better fit, with KS values approximately half the Rayleigh KS values. No significant trends were observed in the goodness of fit with increased exposure time (Table 3.2).

TABLE 3.2

KS goodness of fit parameter for the Rayleigh and Generalized Gamma distribution fits to data from untreated AML cells and AML cells exposed to cisplatinum for 24 hours. Values represent the mean of four experiments with standard deviation between the experiments. While there is a slight increase in the goodness of fit from 0 to 24 hours (decrease of the KS values), the changes are not significant.

| Treatment Time (hrs) | Rayleigh | GG |
|---|---|---|
| 0 hrs. | 0.02 ± 0.01 | 0.011 ± 0.004 |
| 24 hrs. | 0.01 ± 0.01 | 0.006 ± 0.004 |

Figure 14:
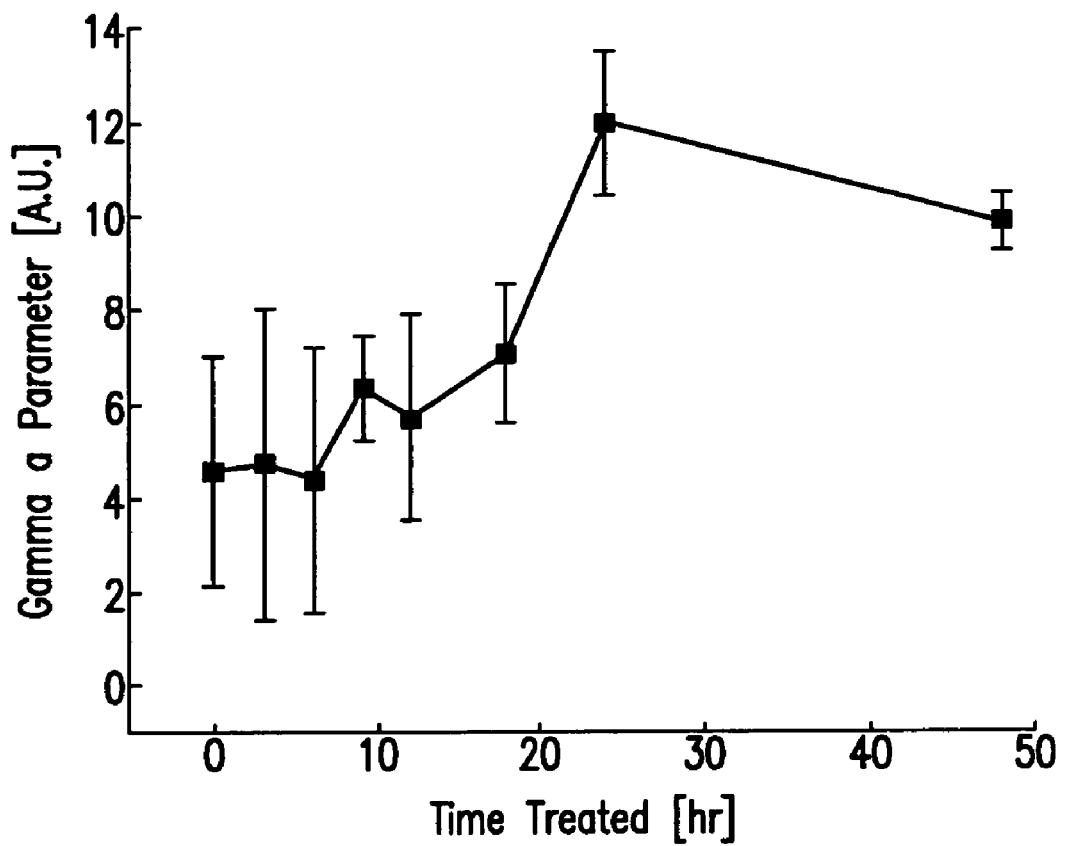
FIG. 14 shows the GG a parameter with standard deviations for ultrasound data from pellets of cells treated with cisplatinum for 0 to 48 hours shows a large increase between the untreated cells and cells treated for 24 hours. This corresponds to the approximately 13 dB increase in IB and the change in the mean of the histogram.
Figure 15:
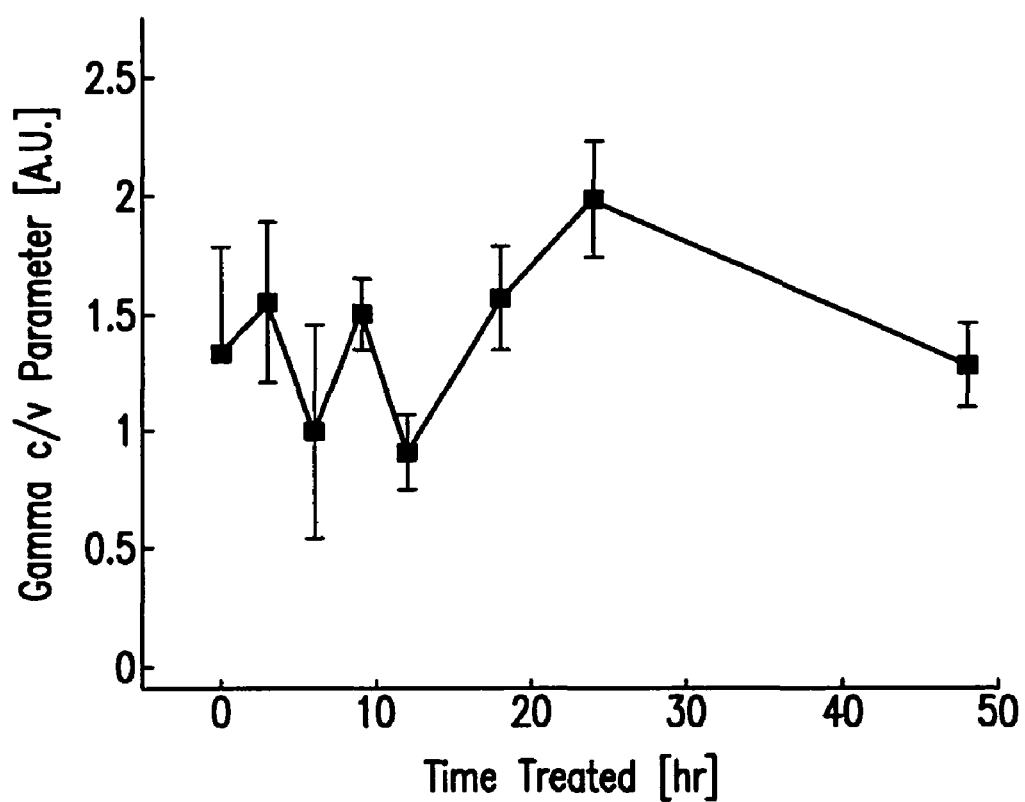
FIG. 15 shows the GG c/v parameter with standard deviations for ultrasound data from pellets of cells treated for 0 to 48 hours with cisplatinum shows large variability at early timepoints between the four experiments. There is an increasing trend between 12 and 24 hours, consistent in all four experiments and coincident with the steep changes in IB.

The GG a parameter increased consistently for the samples treated from 0 through 24 hours for all the experiments performed (FIG. 14). The ratio of the GG c/v parameters showed large variability between the four experiments in the values for samples treated for a short time, up to 12 hours, however all the data showed an increasing trend over the period from 12 to 24 hours (FIG. 15). This coincides with the largest changes observed in IB. The consistent increase in c/v between 12 and 24 hours for all experiments indicate an increase in effective scatterer number density (FIG. 10).

To demonstrate the sensitivity of the signal statistics to changes in a small percentage of a cell population, pellets of mixed populations of cells were prepared. In a clinical treatment, there may be a very small number of cells within the tissue responding to treatment.

The AML cells treated for 24 hours in the timecourse showed a large proportion of cells with condensed nuclei, the largest changes in the GG fit parameters and a maximum increase in IB of 13 dB also occurred at 24 hours. We therefore similarly prepared AML cells treated for 24 hours with 10 μg/ml of cisplatinum. The treated cells were then mixed with untreated cells to form mixtures containing 0%, 2.5%, 5%, 10%, 20%, 40%, 60%, 80% and 100% treated cells, and then centrifuged in a swinging bucket centrifuge for 10 minutes at 2000 g to form pellets. The pellets were immersed in PBS which served as a coupling medium between the pellet and the transducer (FIG. 11). Several B-scan images were saved and RF data were acquired from approximately 200 locations separated by at least one beamwidth within the pellet. Following the data acquisition the pellets were fixed and Haemotoxylin and Eosin (H&E) staining was performed to examine structural changes in the cells. Using the model of Hunt et al. Ultrasound Med. Biol, 28(2), 2002, simulations were performed to model the ultrasound backscatter of pellets containing a mixed population of treated and untreated cells. Based on histological observations, the modeled untreated cells had a nuclear diameter of 90% the cell's diameter. The treated cells were modeled as having a nucleus condensed to 40% of the cell's diameter. The amplitude of the modeled signal was scaled so the IB from untreated cells matched the IB obtained experimentally from pellets of untreated cells using the ultrasound system.

Figure 17:
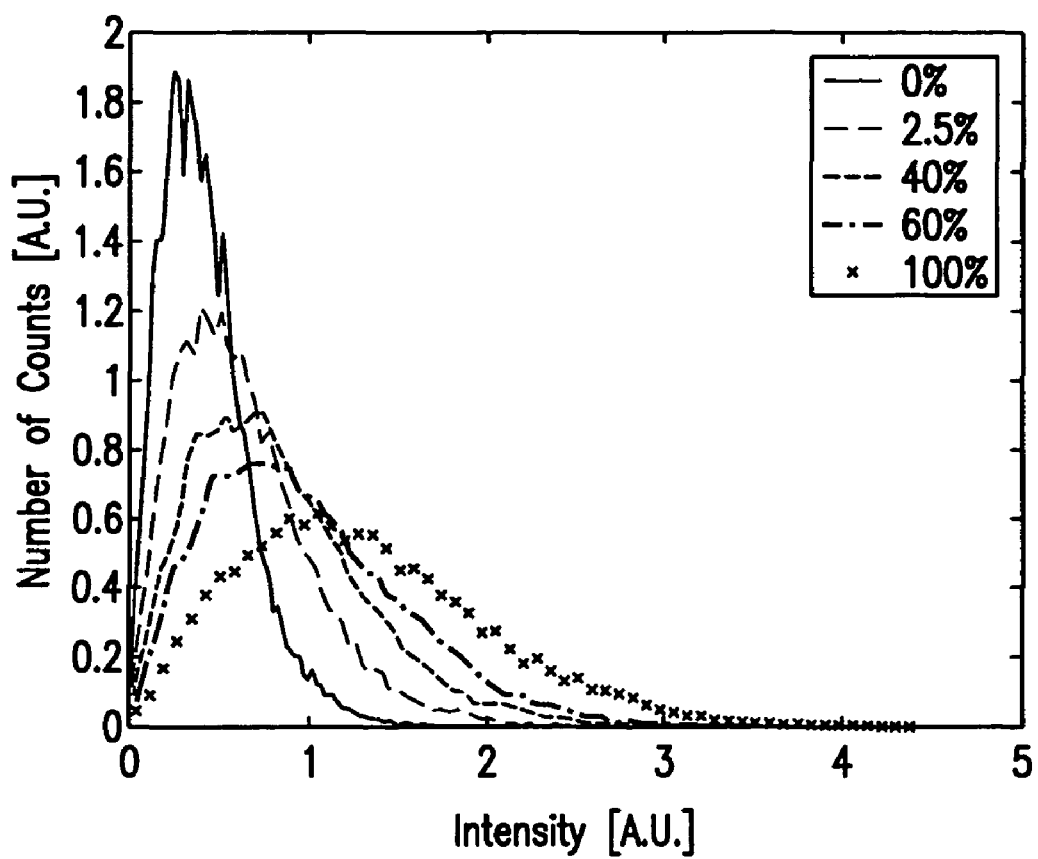
FIG. 17 shows histograms for ultrasound data acquired from pellets of cells formed with varying mixtures of AML cells treated with cisplatinum. The large change in scale corresponds to the increase in IB. There are also more subtle changes to the shape of the histograms as the concentration of treated cells increases.
Figure 18:
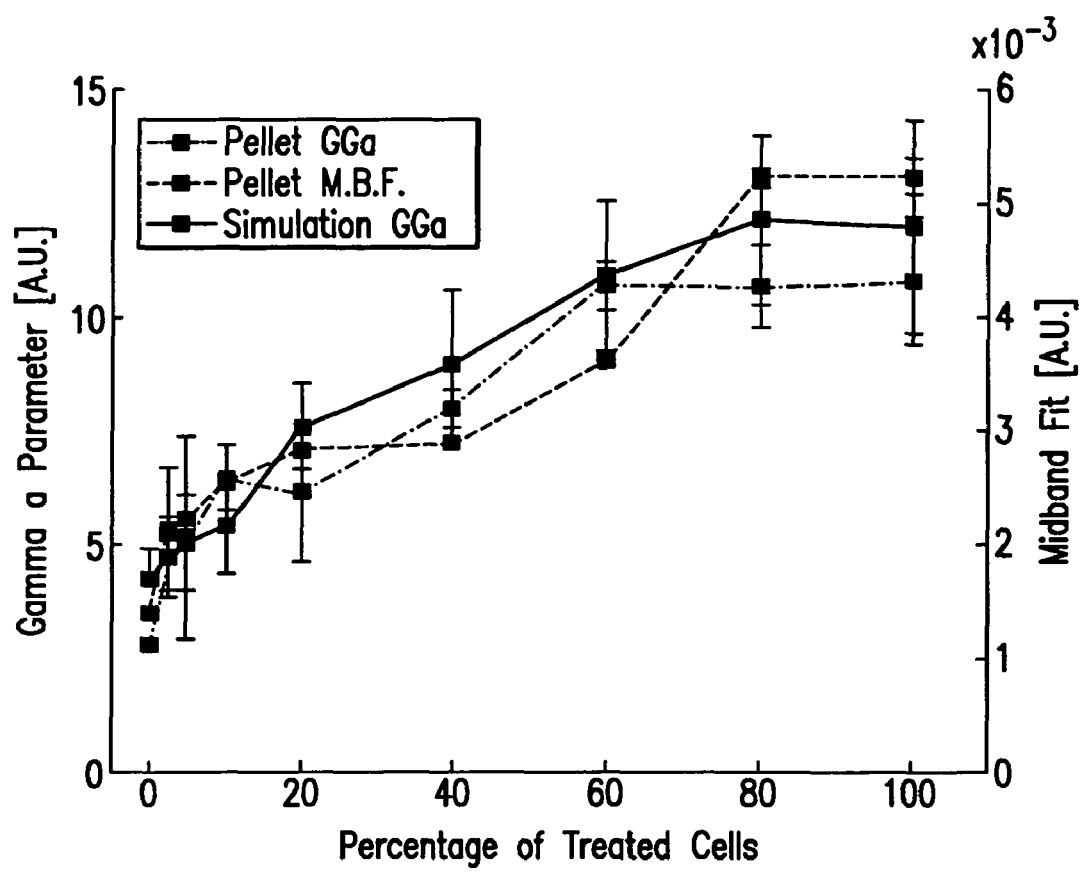
FIG. 18 shows the GG a parameter with 95% confidence intervals for ultrasound data from cell pellets and simulations of mixtures of treated and untreated AML cells. There is a consistent increase in the a parameter as the concentration of treated cells increases, with general agreement between experiment and simulation. A similar increase is observed in the IB (plotted on the right axis).
Figure 19:
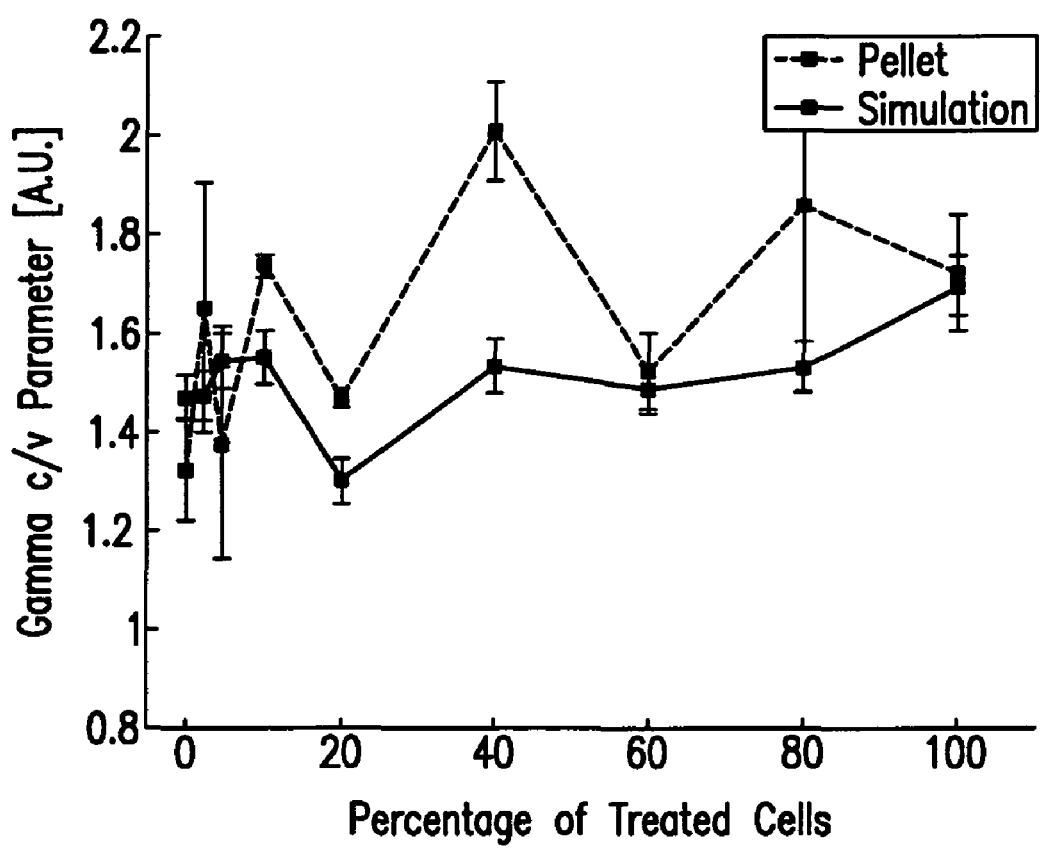
FIG. 19 shows the GG c/v parameter with 95% confidence intervals for ultrasound data from cell pellets and simulations of mixtures of treated and untreated AML cells. Similar non-monotonic changes were observed as the concentration of treated cells increased in both the experimental and simulated data.
Figure 20A:
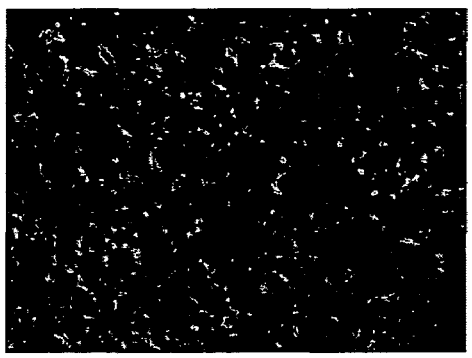
FIG. 20 shows representative H&E histology of NHL tumors before (A) and 12 hours post (B) treatment with CHOP chemotherapy regimen. Structural changes are visible in the treated section. B-scan images of the same tumor with a 20 MHz f#2.35 transducer show an increase in intensity in the treated tumor (C-D). Note scanning direction is reversed in (D).
Figure 20B:
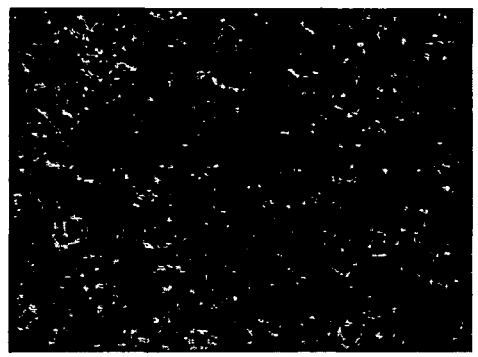
Figure 20C:
Figure 20D:

The corresponding B-scan images show an increase in the backscatter intensity for pellets formed with a higher concentration of treated cells. Despite logarithmic compression an increase in brightness is visible between the B-scan images of pellets formed with 0% and 2.5% treated cells (FIG. 16). This increase in brightness corresponds to an increase in IB of approximately 3 dB. As the percentage of treated cells in the pellet was increased the signal intensity increased, producing large changes to the shape of the histogram (FIG. 17). Based on the KS goodness of fit the Rayleigh and GG distribution both provided fits to the empirical and simulated data for all mixtures of treated and untreated cells. Again the GG provided a better fit and there were no apparent trends in the KS values with mixture composition. The GG scale parameter showed an increased as the percentage of treated cells was increased, corresponding to an increase in the MBF of approximately four times (~12 dB) (FIG. 18). The GG a parameter for the simulated data shows a similar trend. The ratio of the parameters c/v showed fluctuations as the percentage of treated cells increased (FIG. 19). While the GG a parameter is sensitive to the scaling applied to the simulated data, the GG c/v ratio is independent of this scaling factor. There is general agreement between the GG c/v ratio of the experimental data and the simulated data, with both showing similar values.

Ultrasound data were collected from dilute suspensions of AML and PC cells to assess the physical interpretation of the GG fit parameters. The results demonstrate that the GG fit parameters can be related to physical properties of scatterers in a cell system. The parameter depends on the effective scatterer cross-section (FIG. 9), and the ratio of c/v depends on the effective scatterer number density (FIG. 10). This was confirmed in the experimental results, indicating that effective scatterer cross-section and number density can be evaluated using signal statistics from sparse solutions of cells.

In the pellets of AML and PC-3 cells, similar trends are observed, the larger cells (PC-3) have a higher scale parameter, corresponding to a larger effective cross-section. The smaller cells (AML) have a higher ratio of c/v, corresponding to the higher number density of cells in a pellet. The difference in the parameters between the suspensions and pellets of the same cells indicates that there is a different scattering interaction in cells in suspension and pellets of cells. Increased randomization leads to an increase in the GG a parameter. The decreased randomization in the pellet compared to the solution produces the large difference observed in the GG parameters between the pellets and solutions of cells (FIGS. 9 and 10). Thus these parameters provide a measure of effective scatterer cross-section and number density. The parameters are related to physical properties of scatterers, and they can be used to monitor changes in scatterer properties.

To assess the effect of changes in cell structure on signal statistics, data were collected from pellets of AML cells treated for different times with cisplatinum. To assess the lower limit of detection data were also collected from pellets containing mixtures of treated and untreated AML cells. Simulated data were generated to model the data acquired from pellets containing a mixture of cells. Based on the KS fit test both PDFs provided reasonable fits to the cell pellet data. However the GG distribution provided a significantly better fit than the Rayleigh distribution. This was true for both the experimental and simulated data.

The GG a parameter increased for cells treated for a longer time. The ratio of the shape parameters (c/v) of the GG distribution also showed a consistent increase from 12 to 24 hours of treatment in all four experiments. These changes coincide with the large increase in IB observed at 24 hours. Similar results were obtained from the mixtures of treated and untreated cells. Both a and the ratio c/v increased as the concentration of treated cells increased with reasonable agreement between the experimental and simulated data. The large changes observed in the parameters from pellets containing low concentrations of treated cells indicates that structural changes can be detected within a small percentage of a population of cells. This is particularly relevant for clinical applications, as there may be a very low percentage of cells responding to treatment at any one point in time.

As well the actual sensitivity is lower than 2.5%. Even in an in vitro model the actual number of cells responding to treatment is not 100%. As such in a pellet formed with 2.5% treated cells, fewer than 2.5% of the cells undergo changes as a result of the treatment.

During treatment of the AML cells with cisplatinum there are a number of structural changes to the nucleus, however the spacing between nuclei remains relatively constant as evidenced by histology (FIGS. 12 & 16). A similar increase was observed in c/v for the simulated data where the number density of scatterers is kept constant through the range of situations modeled. This indicates that randomization affects the effective scatterer number density. All three GG fit parameters showed large changes for pellets formed with between 0% and 20% treated cells.

The results demonstrate that signal statistics are affected by physical properties of cells. Data from dilutions of AML and PC-3 cells demonstrated that the GG a and c/v parameters can be related to the effective scatterer cross-section and number density respectively.

Example 5

The in vitro results demonstrated that signal envelope statistics are sensitive to structural changes in cells. To monitor tumor response to therapy in vivo the application of envelope statistics analysis to monitoring the response of a tumor to treatment was evaluated the response of non-Hodgkin's lymphoma (NHL) tumors implanted in mice and treated with the CHOP chemotherapy regimen.

Non-Hodgkin's Lymphoma cells (CRL2261, American Tissue Culture Collection) were cultured, then a concentration of $10^6$ cells in 50 μl of media was injected intradermally into the left hind leg of severe combined immunodeficiency disease (SCID) mice. Primary tumors were allowed to develop for approximately 4 weeks, until they reached a diameter of 8-10 mm. The mice were treated with the CHOP chemotherapy regimen, as is used clinically to treat aggressive NHL. In this regimen four drugs (Cyclophosphamide, Hydroxydoxorubicin, Vincristine (Oncovin) and Prednisone) are injected with a 15 minute separation between drugs. Prednisone is injected daily during the treatment, while the other drugs are injected only at the beginning of the treatment. As a control, other animals received injections of saline following the same injection procedure as the treated animals.

Prior to the imaging procedure the hair on the tumor was removed with a depilatory (Neet™, Reckitt-Benckiser, UK). The animals were then anaesthetized for the imaging procedure. For most procedures a mixture of drugs (100 mg/kg Ketamine, 5 mg/kg Xylasine and 1 mg/kg Acepremazine diluted with saline to 0.1 μml) was injected subcutaneously as this sedated the mouse for approximately 1.5 hours, sufficient time for the entire imaging procedure. However when imaging was performed at multiple times for the same animal an inhaled anaesthetic (halothane) was administered to reduce the stress on the animal of multiple injections at short time intervals. The mouse was placed in a specially designed restraint which held the tumor submerged in a heated water bath but elevated the head out of the water. The transducer was scanned linearly across the tumor. Care was taken to scan the same region at all timepoints. Histological sections were taken from the scanned region of the tumor in the same plane as the images. The tumors of 12 animals were each imaged before the treatment and at time points up to 96 hours after the beginning of the treatment. The tumors of four additional mice were imaged at multiple timepoints during the treatment, to monitor the changes as they occurred within one animal. B-scan images and RF data were acquired from the tumor using the 20 MHz f#2.35 transducer. Approximately 200 RF lines separated by at least one beamwidth were acquired from five imaging planes within the tumor. Care was taken to ensure the imaging procedure was performed in the same region of the tumor at all time points during the treatment. Animals were sacrificed at various time points and tumor tissue was extracted and fixed for H&E and TUNEL staining.

Figure 21:
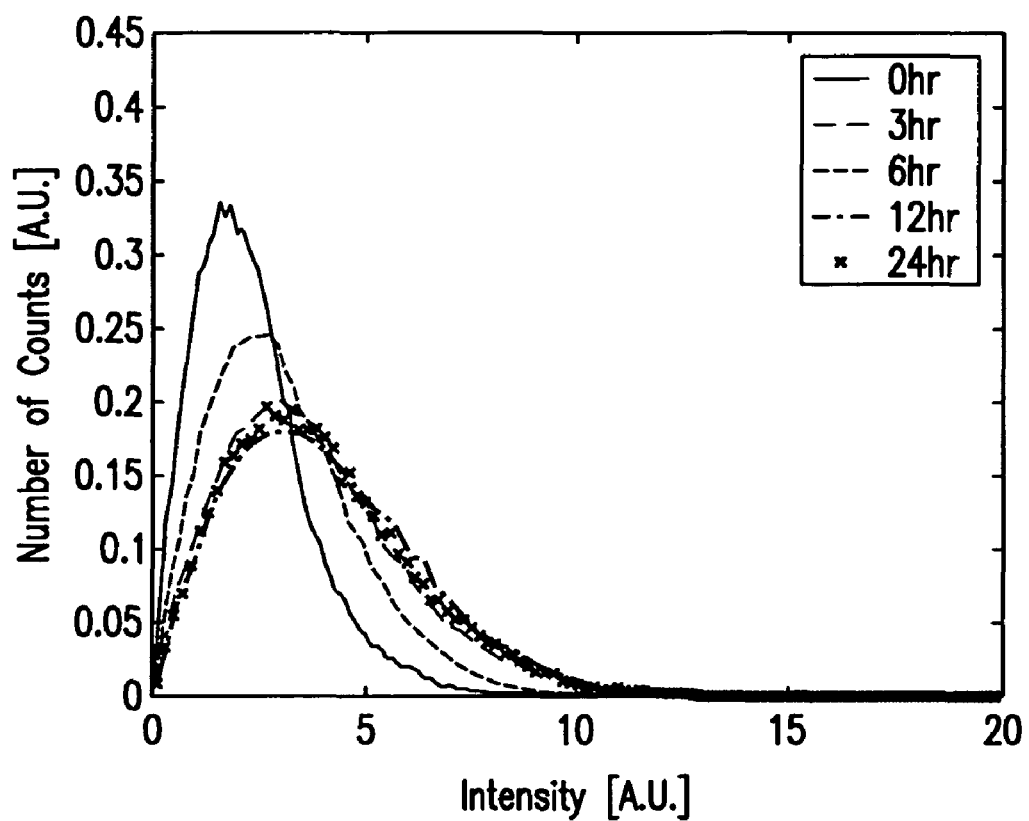
FIG. 21 shows histograms for ultrasound data acquired from a NHL tumor in a single mouse over 24 hours of CHOP chemotherapy treatment. The large change in scale corresponds to the increase in IB or mean intensity.

Representative histology from the treated NHL tumors shows a number of cells with visible structural changes including condensation of the nucleus and cytoplasmic disruption (FIG. 20). These results are fairly typical of most of the histology, where significant changes became apparent histologically after about 12 hours of treatment. The B-scan images taken from one animal before and 12 hours after treatment display an observable increase in the backscatter intensity after treatment. The maximum increase in B-scan intensity was typically observed approximately 12 hours after treatment. For clarity, histograms and fit parameters for one representative animal are presented first, followed by results from a number of animals. Similar to the in vitro experiments, the changes in intensity observed in the B-scan images are reflected in the shape of the histogram of the signal amplitude (FIG. 21). As well after approximately 12 hours, the shape of the histogram remained fairly consistent until approximately 30 hours. The KS goodness of fit values indicate that the GG PDF achieved significantly better values (0.016±0.006 before treatment) to the data than the Rayleigh PDF (0.10±0.05 before treatment). No significant trends were observed in the KS values with treatment time. While the changes observed to the shape of the histogram are minor after 12 hours, inspection of the GG fit parameters reveals trends that are not immediately visible (FIG. 22). In the fit parameters a maximum change is observed after only 6 hours, and the values, in particular the ratio c/v, return to very near the initial levels after 48 hours. The values of the GG fit parameters varied between animals. This is demonstrated by the large standard deviations compared to the average parameter values for the tumors before treatment (Table 4.2).

TABLE 4.2

Mean and standard deviation of the Generalized Gamma fit parameters determined from 12 different tumours before treatment.

| GG a [Arb.U.] | GG c [Arb.U.] | GG v [Arb.U.] | GG c/v [Arb.U.] |
|---|---|---|---|
| 1.0 ± 0.9 | 0.9 ± 0.3 | 4.0 ± 2.9 | 0.4 ± 0.2 |

To make comparisons of the results from all the animals, the values of parameters relative to the initial value was examined.

Figure 23B:
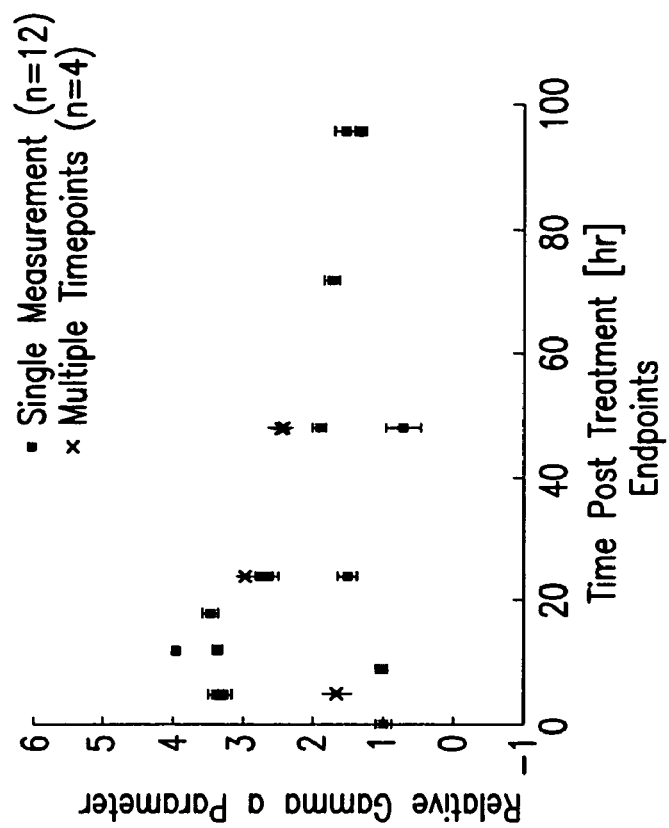
FIG. 23 shows the relative GG a parameter with 95% confidence intervals for ultrasound data from NHL tumors. Four animals were imaged at multiple timepoints post treatment (A). The values shown are normalized to the pre-treatment measurement and each line represents one animal. Twelve animals were imaged at predetermined timepoints following treatment then sacrificed for histology (B). Each square marker represents one animal and the crosses represent the final timepoints for the four animals from (A). The increase in the GG a parameter peaking at 12 hours post treatment corresponds to the maximum increase in IB observed. A relative increase of 4 in the GG a parameter corresponds to an increase in IB of approximately 8 dB.
Figure 23A:
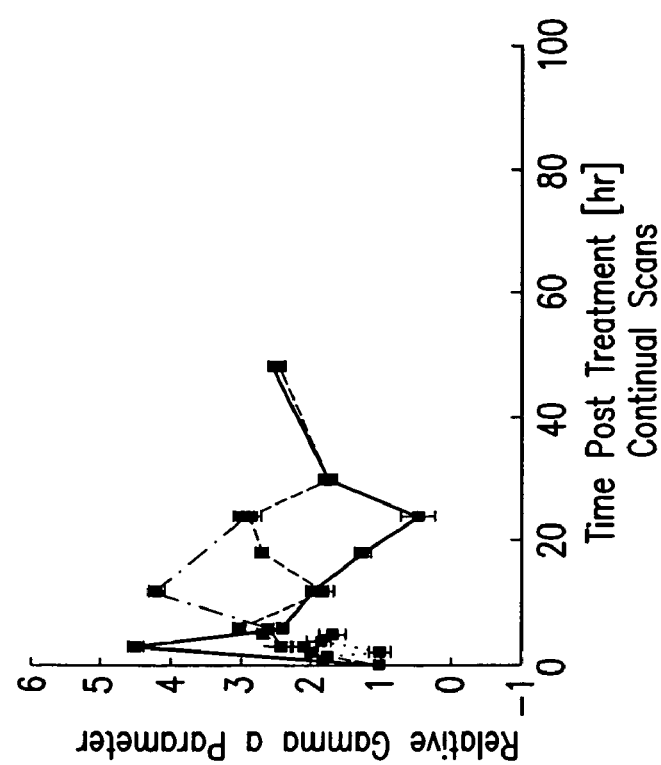
Figure 24B:
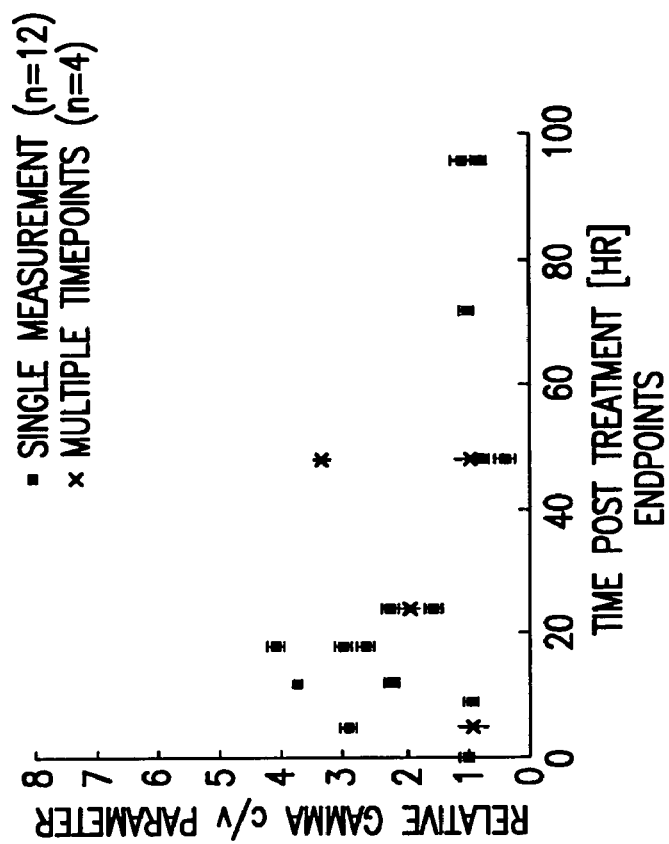
FIG. 24 shows the relative GG c/v parameters with 95% confidence intervals for ultrasound data from NHL tumors. Four animals were imaged at multiple timepoints post treatment (A). The values shown are normalized to the pre-treatment measurement and each line represents one animal. Twelve animals were imaged at predetermined timepoints following treatment then sacrificed for histology (B). Each square marker represents one animal and the crosses represent the final timepoints for the four animals from (A). The ratio of c/v reaches a maximum at 12 hours, decreasing to original levels at later times.
Figure 24A:
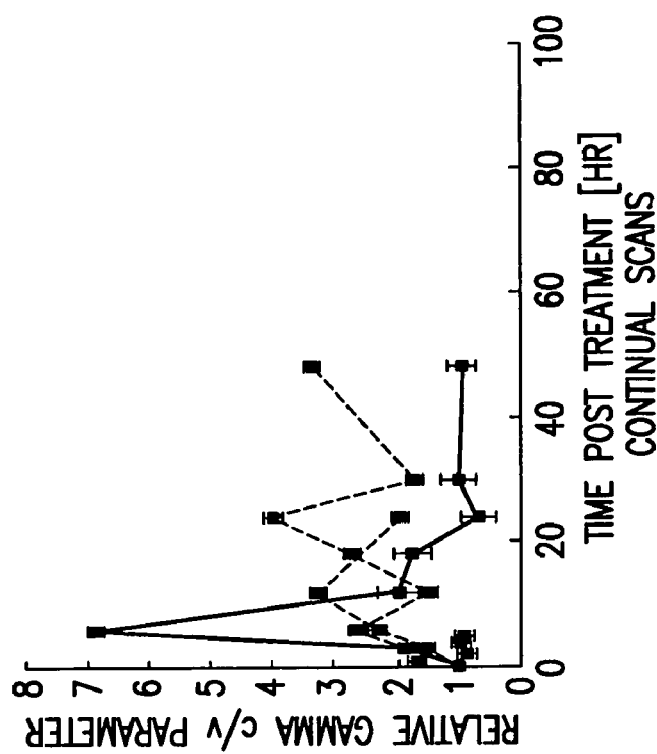
Figure 25:
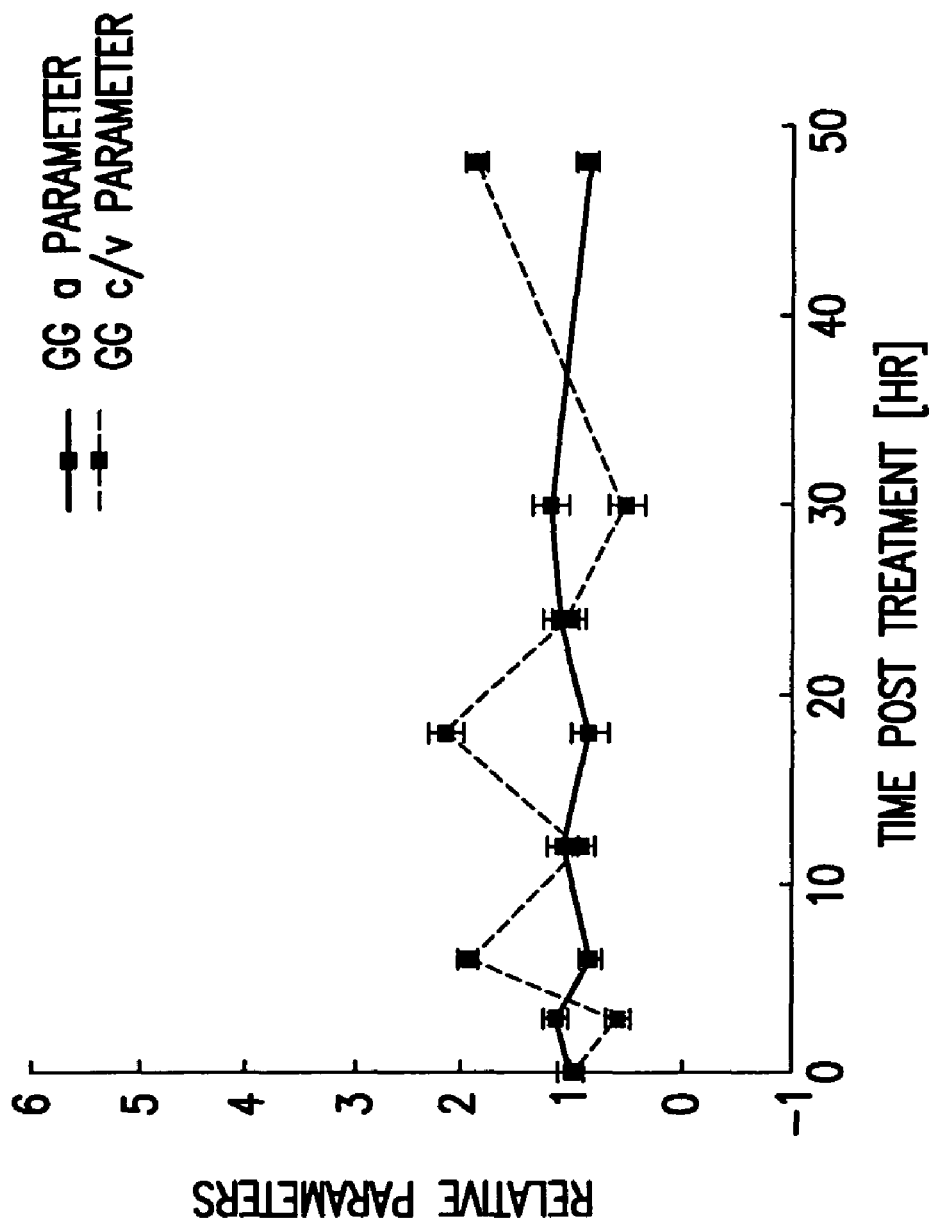
FIG. 25 shows Generalized Gamma fit parameters with 95% confidence intervals for ultrasound backscatter data collected from one untreated NHL tumor scanned at several timepoints over 48 hours.

For all the treated animals the GG a parameter increased at all times after the beginning of the treatment. A maximum increase of up to 300% was observed at 12 hours of treatment (FIG. 23). At later times the GG a parameter decreased again to levels slightly above the initial values. The ratio of the GG c/v parameters also showed a large increase at early time points relative to the initial values. A maximum increase of approximately 250% of the original value occurred at 12 hours post treatment, diminishing at later times to insignificant deviations 72 and 96 hours post treatment (FIG. 24). The changes in these parameters indicate an increase in both the effective scatterer cross-section and the effective scatterer number density, reaching a maximum between 12 and 24 hours of treatment. In contrast to the trends observed in treated tumors, examination of animals imaged without any treatment do not show any discernible trends (FIG. 25). There are however fairly large fluctuations in the values of the parameters through out the examination period, 48 hours for the animal in FIG. 25. In particular for the ratio of c/v the fluctuations are significantly larger than the 95% confidence intervals. The fluctuations of the a parameter are closer to the level of the 95% confidence intervals. This indicates that the variability of the parameters within one tumor as a function of time is quite high.

Example 6

Figure 30:
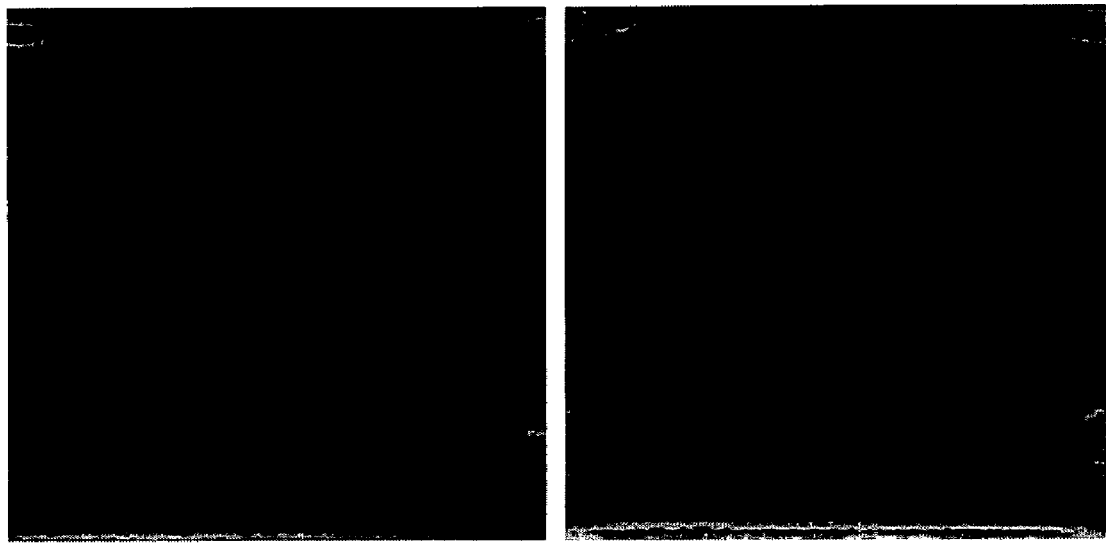
FIG. 30 shows results of apoptotic analysis with low-frequency ultrasound.

FIG. 30 shows results of apoptotic analysis with low-frequency ultrasound. Panels show 2 cm by 2 cm images of prepared AML (acute myeloid leukemia cells) centrifuged at 4,500×g and submersed in phosphate buffered saline pH 7.4. The left panel is a 5 MHz image of viable untreated cells whereas the right panel is an image at the same frequency of AML cells treated with cisplatinum for 24 hours which has caused apoptosis as before. The echoes at the top left and top right of each image are reflections from the wise walls of the specimen chamber. The intensity of the apoptotic cells is increased 4-8 fold compared to the untreated cells.

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

REFERENCES

[1] R. E. Baddour, M. D. Sherar, J. W. Hunt, G. J. Czarnota, and M. C. Kolios. High frequency ultrasound scattering from microspheres and single cells. *J Acoust Soc Am, In Press*.

[2] J. W. Hunt, A. E. Worthington, A. Xuan, M. C. Kolios, G. J. Czamota, and M. D. Sherar. A model based upon pseudo regular spacing of cells combined with the randomisation of the nuclei can explain the significant changes in high-frequency ultrasound signals during apoptosis. *Ultrasound Med Biol*, 28(2):217-26, 2002.

[3] Christopher J. Harvey, James M. Pilcher, Robert J. Eckersley, Martin J. K. Blomley, and David O. Cosgrove. Advances in ultrasound. *Clin Radiol*, 90(3):157-177, 2002.

[4] M. D. Sherar, M. B. Noss, and F. S. Foster. Ultrasound backscatter microscopy images the internal structure of living tumour spheroids. *Nature*, 330(6147):493-5, 1987.

[5] M. D. Sherar, B. G. Starkoski, W. B. Taylor, and F. S. Foster. A 100 mhz b-scan ultrasound backscatter microscope. *Ultrason Imaging*, 11(2):95-105, 1989.

[6] F. S. Foster, C. J. Pavlin, K. A. Harasiewicz, D. A. Christopher, and D. H. Turnbull. Advances in ultrasound biomicroscopy. *Ultrasound Med Biol*, 26(1):1-27, 2000.

[7] L. R. Berube, K. Harasiewicz, F. S. Foster, E. Dobrowsky, M. D. Sherar, and A. M. Rauth. Use of a high frequency ultrasound microscope to image the action of 2-nitroimidazoles in multicellular spheroids. *Br J Cancer*, 65(5):633-40, 1992.

[8] M. C. Kolios, G. J. Czarnota, M. Hussain, F. S. Foster, J. W. Hunt, and M. D. Sherar. Analysis of ultrasound backscatter from ensembles of cells and isolated nuclei. In *IEEE Ultrasonics Symposium*, volume 2, pages 1257-1260, 2001.

[9] G. J. Czarnota, M. C. Kolios, H. Vaziri, S. Benchimol, F. P. Ottensmeyer, M. D. Sherar, and J. W. Hunt. Ultrasonic biomicroscopy of viable, dead and apoptotic cells. *Ultrasound Med Biol*, 23(6):961-5, 1997.

[10] G. J. Czarnota, M. C. Kolios, J. Abraham, M. Portnoy, F. P. Ottensmeyer, J. W. Hunt, and M. D. Sherar. Ultrasound imaging of apoptosis: high-resolution non-invasive monitoring of programmed cell death in vitro, in situ and in vivo. *Br J Cancer*, 81(3):520-7, 1999.

[11] G. J. Czarnota, M. C. Kolios, J. W. Hunt, and M. D. Sherar. Ultrasound imaging of apoptosis. Damage effects visualized. *Methods Mol Biol*, 203:257-77, 2002.

[12] M. C. Kolios, G. J. Czarnota, M. Lee, J. W. Hunt, and M. D. Sherar. Ultrasonic spectral parameter characterization of apoptosis. *Ultrasound Med Biol*, 28(5):589-97, 2002.

[13] M. A. Barry, C. A. Behnke, and A. Eastman. Activation of programmed cell death (apoptosis) by cisplatin, other anticancer drugs, toxins and hyperthermia. *Biochem Pharmacol*, 40(10):2353-62, 1990.

[14] M. L. Oelze and Jr. O'Brien, W. D. Method of improved scatterer size estimation and application to parametric imaging using ultrasound. *J Acoust Soc Am*, 112(6):3053-63, 2002.

[15] M. L. Oelze, J. F. Zachary, and Jr. O'Brien, W. D. Parametric imaging of rat mammary tumors in vivo for the purposes of tissue characterization. *J Ultrasound Med*, 21(11): 1201-10, 2002.

[16] Michael L. Oelze, James F. Zachary, and Jr. O'Brien, William D. Differentiation of tumor types in vivo by scatterer property estimates and parametric images using ultrasound backscatter. In *IEEE Trans Ultrason Ferroelectr Freq Control*, Honolulu, Hi., 2003. IEEE.

[17] M. C. Kolios, L. Taggart, R. E. Baddour, F. S. Foster, J. W. Hunt, G. J. Czarnota, and M. D. Sherar. An investigation of backscatter power spectra from cells, cell pellets and microspheres. In *IEEE Ultrasonics Symposium*, pages 752-757, Honolulu, Hi., 2003.

[18] P. M. Shankar, J. M. Reid, H. Ortega, C. W. Piccoli, and B. B. Goldberg. Use of non-rayleigh statistics for the identification of tumors in ultrasonic b-scans of the breast. *IEEE Trans Med Imaging*, 12(4):687-692, 1993.

[19] P. M. Shankar. A model for ultrasonic scattering from tissues based on the k distribution. *Phys Med Biol*, 40(10): 1633-49, 1995.

[20] P. M. Shankar, R. Molthen, V. M. Narayanan, J. M. Reid, V. Genis, F. Forsberg, C. W. Piccoli, A. E. Lindenmayer, and B. B. Goldberg. Studies on the use of non-rayleigh statistics for ultrasonic tissue characterization. *Ultrasound Med Biol*, 22(7):873-82, 1996.

[21] P. M. Shankar. A compound scattering pdf for the ultrasonic echo envelope and its relationship to k and nakagami distributions. *IEEE Trans Ultrason Ferroelectr Freq Control*, 50(3):339-343, 2003.

[22] P. M. Shankar, V. A. Dumane, J. M. Reid, V. Genis, F. Forsberg, C. W. Piccoli, and B. B. Goldberg. Classification of ultrasonic b-mode images of breast masses using nakagami distribution. *IEEE Trans Ultrason Ferroelectr Freq Control*, 48(2):569-80, 2001.

[23] P. M. Shankar, V. A. Dumane, T. George, C. W. Piccoli, J. M. Reid, F. Forsberg, and B. B. Goldberg. Classification of breast masses in ultrasonic b scans using nakagami and k distributions. *Phys Med Biol*, 48(14):2229-40, 2003.

[24] X. Hao, C. J. Bruce, C. Pislaru, and J. F. Greenleaf. Segmenting high-frequency intracardiac ultrasound images of myocardium into infarcted, ischemic, and normal regions. *IEEE Trans Med Imaging*, 20(12):1373-83, 2001.

[25] B. I. Raju and M. A. Srinivasan. Statistics of envelope of high-frequency ultrasonic backscatter from human skin in vivo. *IEEE Trans Ultrason Ferroelectr Freq Control*, 49(7):871-82, 2002.

[26] J. Beaulieu, R. Vlad, L. Taggart, Y. M. Heng, A. Giles, M. D. Sherar, J. W. Hunt, G. J. Czarnota, and M. C. Kolios. High-frequency ultrasound characterization of microcellular components. In *Proceedings of the 10$^{th}$ Congress of the World Federation for Ultrasound in Medicine and Biology*, page S123, Montreal, Canada, 2002.

[27] G. J. Czarnota. Ultrasound imaging of apoptosis in vivo: Effects of subcellular nuclear morphology and cell membrane morphology. In *Proceedings of the 10$^{th}$ Congress of the World Federation for Ultrasound in Medicine and Biology*, page S117, Montreal, Canada, 2002.

[28] M. C. Kolios, G. J. Czarnota, A. E. Worthington, A. Giles, A. S. Tunis, and M. D. Sherar. Towards understanding the nature of high frequency backscatter from cells and tissues: An investigation of backscatter power spectra from different concentrations of cells of different sizes. In *IEEE Ultrasonics Symposium*, Montreal, Canada, 2004.

[29] J. W. Strutt. Investigation of the disturbance produced by a spherical obstacle on the waves of sound. *Proceedings of the London Mathematical Society*, 4:233-283, 1872.

[30] James J. Faran. Sound scattering by solid cylinders and spheres. *J Acoust Soc Am*, 23(4):405-418, 1951.

[31] Ralph Baddour. High frequency ultrasound scattering from microspheres and single cells. Master's thesis, University of Toronto, 2004.

[32] J. W. Strutt. On the resultant of a large number of vibrations of the same pitch and of arbitrary phase. *Phil Mag S5*, 10(60):73-78, 1880.

[33] Vinayak Dutt. *Statistical Analysis of Ultrasound Echo Envelope*. PhD thesis, Mayo Graduate School, 1995.

[34] E. W. Stacy. A generalization of the gamma distribution. *The Annals of Mathematical Statistics*, 33(3):1187-1192, 1962.

[35] P. M. Shankar. Ultrasonic tissue characterization using a generalized nakagami model. *IEEE Trans Ultrason Ferroelectr Freq Control*, 48(6):1716-1720, 2001.

[36] L. Y. Mo and R. S. Cobbold. A unified approach to modeling the backscattered doppler ultrasound from blood. *IEEE Trans Biomed Eng*, 39(5):450-61, 1992.

[37] V. Dutt and J. F. Greenleaf. Ultrasound echo envelope analysis using a homodyned k distribution signal model. *Ultrason Imaging*, 16(4):265-87, 1994.

[38] William H. Press, Saul A. Teukolsky, William T. Vetterling, and Brian P. Flannery. *Numerical Recipes in FORTRAN: The art of scientific computing*, 2$^{nd}$ ed. Cambridge University Press, New York, 2 edition, 1992.

[39] Jagdish K. Patel, C. H. Kapadia, and D. B. Owen. *Handbook of statistical distributions*. Statistics, textbooks and monographs v 20. M. Dekker, New York, 1976.

[40] R. C. Molthen, P. M. Shankar, J. M. Reid, F. Forsberg, E. J. Halpern, C. W. Piccoli, and B. B. Goldberg. Comparisons of the rayleigh and k-distribution models using in vivo breast and liver tissue. *Ultrasound Med Biol*, 24(1):93-100, 1998.

[41] A. S. Tunis, D. Spurrell, D. McAlduff, A. Giles, M. Hariri, R. Khokha, M. D. Sherar, G. J. Czarnota, and M. C. Kolios. High frequency ultrasound signal statistics from mouse mammary tissue during involution. In *IEEE Ultrasonics Symposium*, Montreal, Canada, 2004.

[42] X. Hao, C. J. Bruce, C. Pislaru, and J. F. Greenleaf. Identification of reperfused infarcted myocardium from high frequency intracardiac ultrasound images using homodyned k distribution. In *IEEE Ultrasonics Symposium*, pages 1189-92, 2001.

[43] X. Hao, C. J. Bruce, C. Pislaru, and J. F. Greenleaf. Characterization of reperfused infarcted myocardium from high-frequency intracardiac ultrasound imaging using homodyned k distribution. *IEEE Trans Ultrason Ferroelectr Freq Control*, 49(11): 1530-1542, 2002.

What is claimed is:

1. A method of detecting cellular damage in tissue below the skin of a mammalian subject, comprising:
   transmitting ultrasound having a frequency of at, about or between, 17 MHz, 16 MHz, 15 MHz, 14 MHz, 13 MHz, 12 MHz, 11 MHz, 10 MHz, 9 MHz, 8 MHz, 7 MHz, 6 MHz, 5 MHz, 4 MHz, 3 MHz into one or more cells located in tissue below a subject's skin;
   receiving an ultrasound backscatter signal from the one or more cells;
   processing the received ultrasound backscatter signal to provide frequency spectrum and RF envelope statistics data; and
   analyzing the frequency spectrum and RF envelope statistics data to detect cellular damage by measuring a change in a frequency spectrum and RF envelope statistics data of the ultrasound backscatter signal as compared to a frequency spectrum and RF envelope statistics data of a control ultrasound backscatter signal measurement and correlating a change with cellular damage.

2. The method of claim 1, further comprising exposing the cell to a stress capable of causing cellular damage prior to the transmission of ultrasound into the cell and to the receipt of the ultrasound backscatter signal from the cell.

3. The method of claim 1, wherein the change is an increase in: 1) at least one of a spectral slope, a zero MHz intercept, and a mid-band fit of an average of a normalized frequency spectrum and 2) at least one fit parameter of the RF envelope statistics data, wherein the increase indicates the detection of cellular damage.

4. The method of claim 1, wherein the cellular damage detected is one or more dying cells.

5. The method of claim 4, wherein in the one or more dying cells is undergoing apoptosis or necrosis.

6. The method of claim 1, wherein the cellular damage detected is one or more dead cells.

7. The method of claim 2, wherein the cell is located in a subject and the stress is administered to the cell by radiation therapy, chemotherapy, cryotherapy or brachytherapy.

8. The method of claim 1, wherein the control frequency spectrum ultrasound backscatter signal measurement is taken from a subject prior to administration of the stress capable of causing cellular damage.

9. The method of claim 8, wherein the frequency spectrum ultrasound backscatter signal measurement is taken from the subject subsequent to the taking of the control frequency spectrum ultrasound backscatter signal measurement.

10. The method of claim 1, wherein the step of analyzing the frequency spectrum and RF envelope statistics data to detect cellular damage comprises determining: 1) at least one of the spectral slope, the zero MHz intercept, and the mid-band fit of the average of the frequency spectrum data, and 2) at least one fit parameter of the RF envelope statistic data.

11. The method of claim 10, wherein an increase in: 1) the at least one of the determined spectral slope, the zero MHz intercept and the mid-band fit as compared to at least one of a corresponding control spectral slope, zero MHz intercept, and mid-band fit, and 2) the at least one fit parameter of the RF envelope statistics data as compared to the control indicates the detection of cellular damage.

12. The method of claim 10, wherein a decrease in: 1) the at least one of determined spectral slope and zero MHz intercept as compared to at least one of the control spectral slope and the control zero MHz intercept, and 2) the at least one fit parameter of the RF envelope statistics data compared to the corresponding at least one parameter of control RF envelope statistics data, indicates the detection of cellular damage.

13. The method of claim 11, wherein: 1) the at least one of the control spectral slope, zero MHz intercept, and mid-band fit, and 2) the at least one fit parameter of the RF envelope statistics data are obtained by processing control ultrasound backscatter signal data and wherein the control ultrasound backscatter signal data were received from a subject prior to the administration of a stress capable of causing cellular damage to the subject.

14. The method of claim 1, wherein the step of analyzing the spectral data to detect cellular damage comprises:
   measuring a change in intensity of the ultrasound backscatter signal as compared to the control ultrasound backscatter signal measurement, and wherein an increase in an intensity measurement of the ultrasound backscatter signal as compared to an intensity measurement of the control ultrasound backscatter signal measurement indicates the detection of cellular damage.

15. The method of claim 1, wherein the change is a decrease in: 1) at least one of the slope and the zero MHz intercept of an average of a normalized frequency spectrum, and 2) at least one parameter of the RF envelope statistics data, wherein the decrease indicates the detection of cellular damage.

16. The method of claim 12, wherein: 1) the at least one of the control spectral slope, zero MHz intercept, and mid-band fit, and 2) the at least one fit parameter of the RF envelope statistics data are obtained by processing control ultrasound backscatter signal data and wherein the control ultrasound backscatter signal data were received from a subject prior to the administration of a stress capable of causing cellular damage to the subject.

17. A system for detecting cellular damage in a subject, comprising:
   an ultrasonic transducer configured for transmitting ultrasound at frequency at, about or between, 17 MHz, 16 MHz, 15 MHz, 14 MHz, 13 MHz, 12 MHz, 11 MHz, 10 MHz, 9 MHz, 8 MHz, 7 MHz, 6 MHz, 5 MHz, 4 MHz, 3 MHz into one or more cells located in tissue within the subject below the subject's skin and for receiving an ultrasound backscatter signal from the cell; and
   a processor configured for analyzing the received backscattered data to indicate the detection of cellular damage, the processor being configured to provide spectral and RF envelope statistics data from the received ultrasound backscatter signal and to measure a change in a frequency spectrum and RF envelope statistics data of the ultrasound backscatter signal as compared to a frequency spectrum and RF envelope statistics data of a control ultrasound backscatter signal measurement to indicate the detection of cellular damage.

18. The system of claim 17, wherein the processor is further configured to measure an increase in an intensity measurement of: 1) at least one of spectral slope, zero MHz intercept, and mid-band fit of the average of the normalized frequency spectrum slope, and 2) at least one parameter of the RF envelope statistics data as compared to an intensity measurement of a control spectral and RF envelope statistics data, an increase being indicative of the detection of cellular damage.

19. The system of claim 17, wherein the processor is further configured to measure a decrease in an intensity measurement of: 1) at least one of the spectral slope, zero MHz intercept, and mid-band fit of the average of the normalized frequency spectrum slope, and 2) at least one parameter of the RF envelope statistics data as compared to an intensity measurement of control spectral and RF envelope statistics data, a decrease being indicative of the detection of cellular damage.

20. The method of claim 1, wherein the ultrasound frequency is about 10 MHz.

* * * * *